United States Patent
Che et al.

(10) Patent No.: US 11,286,271 B2
(45) Date of Patent: Mar. 29, 2022

(54) IRIDIUM (III) COMPLEXES CONTAINING N-HETEROCYCLIC CARBENE LIGAND, SYNTHESIS, AND THEIR USE THEREOF IN CANCER TREATMENT

(71) Applicant: The University of Hong Kong, Hong Kong (CN)

(72) Inventors: Chi Ming Che, Hong Kong (CN); Tsz Lung Lam, Hong Kong (CN); Ka Chung Tong, Hong Kong (CN)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 17/264,719

(22) PCT Filed: Jul. 31, 2019

(86) PCT No.: PCT/CN2019/098542
§ 371 (c)(1),
(2) Date: Jan. 29, 2021

(87) PCT Pub. No.: WO2020/024969
PCT Pub. Date: Feb. 6, 2020

(65) Prior Publication Data
US 2021/0317153 A1 Oct. 14, 2021

Related U.S. Application Data

(60) Provisional application No. 62/712,598, filed on Jul. 31, 2018.

(51) Int. Cl.
*C07F 15/00* (2006.01)
*A61K 31/555* (2006.01)
*A61P 35/00* (2006.01)
*A61N 5/06* (2006.01)

(52) U.S. Cl.
CPC .......... *C07F 15/0033* (2013.01); *A61N 5/062* (2013.01); *A61P 35/00* (2018.01)

(58) Field of Classification Search
CPC .... C07F 15/0033; A61K 31/555; A61P 35/00; C07D 487/22
USPC .......................................... 540/465; 514/185
See application file for complete search history.

(56) References Cited

PUBLICATIONS

Anding, B.J. et al.: Comparative study of Rhodium and Iridium porphyrin diaminocarbene and N-heterocyclic carbene complexes. Organometallics, vol. 33, pp. 22219-22229, 2014.*

* cited by examiner

*Primary Examiner* — Charanjit Aulakh
(74) *Attorney, Agent, or Firm* — Pabst Patent Group LLP

(57) ABSTRACT

Provided herein are Ir(III) complexes comprising N-heterocyclic carbene ligand, method of synthesis of the Ir(III) complexes, a pharmaceutical composition comprises thereof. Also provided herein are the methods for the treatment and prevention of cancer/tumor in patients in need thereof by the administration of the Ir(III) complexes under both dark and light conditions. Also provided is a method of detecting the Ir(III) complex in a biological system. Also provided is a method of making the Ir(III) complex. The Ir(III) complexes possess anticancer activity such as the induction of cell death, inhibition of cellular proliferation, and inhibition of tumor growth in vivo.

17 Claims, 12 Drawing Sheets

(A)

(B)

IRIDIUM (III) COMPLEXES CONTAINING N-HETEROCYCLIC CARBENE LIGAND, SYNTHESIS, AND THEIR USE THEREOF IN CANCER TREATMENT

CROSS-REFERENCE TO RELATED APPLICATIONS

This application is a National Phase application under 35 U.S.C. 371 of PCT/CN2019/098542, filed Jul. 31, 2019, and claims the benefit of and priority to U.S. Provisional Application No. 62/712,598, filed Jul. 31, 2018, the disclosures of which are hereby incorporated herein by reference in their entirety.

1. INTRODUCTION

Described herein are iridium (III) complexes containing N-heterocyclic carbene ligand, a method of synthesis of the iridium (III) complexes containing N-heterocyclic carbene ligand, methods of treating and preventing cancer or tumor using the iridium (III) complexes containing N-heterocyclic carbene ligand. The iridium (III) complexes are cytotoxic to tumor growth and/or anti-angiogenesis.

Also provided is a method of detecting the Iridium (III) complexes containing N-heterocyclic carbene ligand by fluorescence microscopy. Also described are therapeutic and prophylactic compositions containing a purified Iridium (III) complexes containing N-heterocyclic carbene ligand. In certain embodiment, the iridium (III) complexes exhibit potent cytotoxicity in the dark. In certain embodiment, the iridium (III) complexes has enhanced cytotoxicity upon light irradiation. In certain embodiments, the methods of treating and preventing cancer or tumor are in combination with other cancer or tumor treatment. In certain embodiments, the cancer or tumor treatment is chemotherapy, radiation therapy, gene therapy, surgery or a combination thereof.

2. BACKGROUND

There are many therapeutics for cancer. The chromophore of iridium based theranostic agent and/or photodynamic agent in the field are dominated by bidentate cyclometalated ligands and diimine ligands. These complexes with bidentate chelates are less stable chemically and photochemically. There are limited number of iridium chelates that have considerable absorption at long wavelength where light is more penetrative to tissue, which is beneficial for theranostic/photodynamic use. Thus, there is a need to provide photodynamic anti-cancer agents that have desirable properties. Photostability, strong light absorption in the visible or red regions and efficient photochemical singlet oxygen generation are important features for the therapeutic compounds. This type of therapeutic compounds can achieve deep tissue penetration, least harmful radiation to healthy tissues, inducing localized cytotoxicity in target tumor tissues by the generated reactive oxygen species (ROS). There is a need for potential photobiological uses of $Ir^{III}$-porphyrin complexes, such as photodynamic therapy. It is important to develop new cytotoxic agents with strong singlet oxygen generation capacity that exhibit potent antitumor activities under dark and light irradiation conditions.

3. SUMMARY

Described herein are Ir(III)-NHC complexes, compositions comprising Ir(III)-NHC complexes, methods of using the Ir(III)-NHC complexes in cancer/tumor treatment, a method of synthesis of Ir(III)-NHC complexes, and a method of detecting the Ir(III)-NHC complexes. In one embodiment, the method of treatment and prevention is in combination with one or more cancer/tumor therapies.

Described herein is a method of synthesis of novel ir(III)-NHC complexes of Structure I, a composition comprising Ir(III)-NHC complexes of Structure I and methods of using the Ir(III)-NHC complexes of Structure I in cancer/tumor treatment under dark and light irradiation conditions.

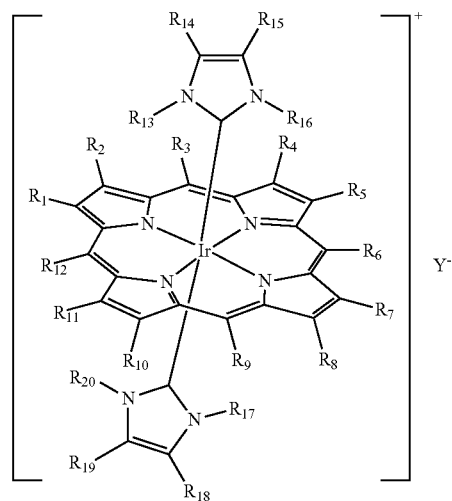

Formula I

The Ir(III)-NHC complex has a structure of formula I, wherein Ir is a iridium center with an oxidation state of III, $R_1$-$R_{20}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group, wherein each pair of adjacent R groups of $R_1$-$R_{20}$ groups can independently form 5-8 member ring(s) and wherein Y is a counter anion selected from $CF_3SO_3$, $PF_6$, $BF_4$, $BPh_4$, $SbF_6$, Cl, Br or I.

In certain embodiments, $R_3$, $R_6$, $R_9$ and $R_{12}$ groups are

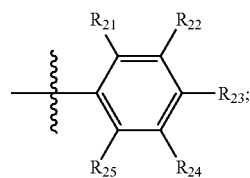

$R_{21}$-$R_{25}$ are independently hydrogen, halogen, unsubstituted alkyl, substituted alkyl, an unsubstituted aryl, a substituted aryl, alkoxy or amino group; $R_1$, $R_2$, $R_4$, $R_5$, $R_7$, $R_8$, $R_{10}$ and $R_{11}$ groups are hydrogen.

In certain embodiments, $R_1$, $R_2$, $R_4$, $R_5$, $R_7$, $R_8$, $R_{10}$ and $R_{11}$ groups are independently halogen, unsubstituted alkyl, substituted alkyl, an unsubstituted aryl, a substituted aryl, alkoxy or amino group; $R_3$, $R_6$, $R_9$ and $R_{12}$ groups are hydrogen.

In certain embodiments,
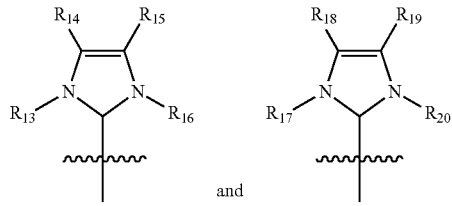
are independently
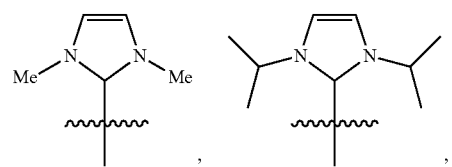
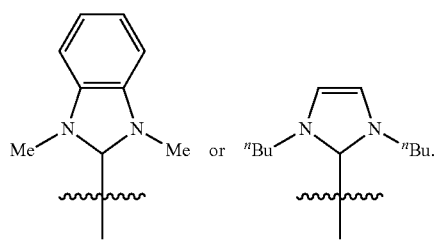
In certain embodiments, the Ir(III) complex comprises the following structures:
Complex 101
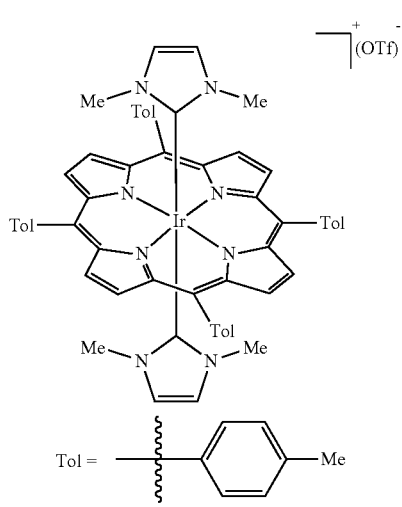
Complex 102
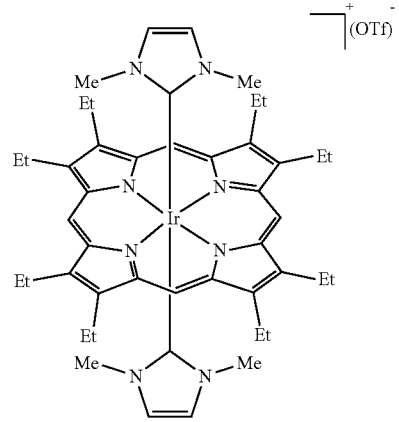
Complex 103
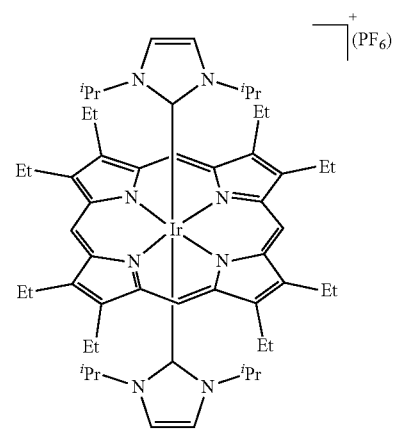
Complex 104
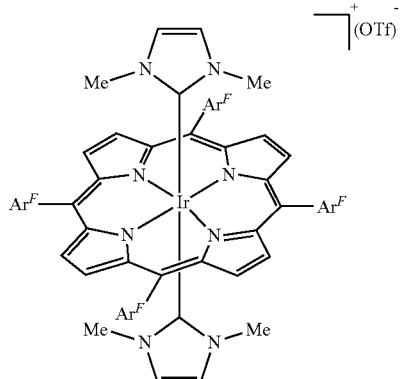
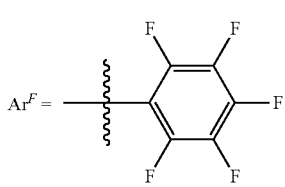

Complex 105
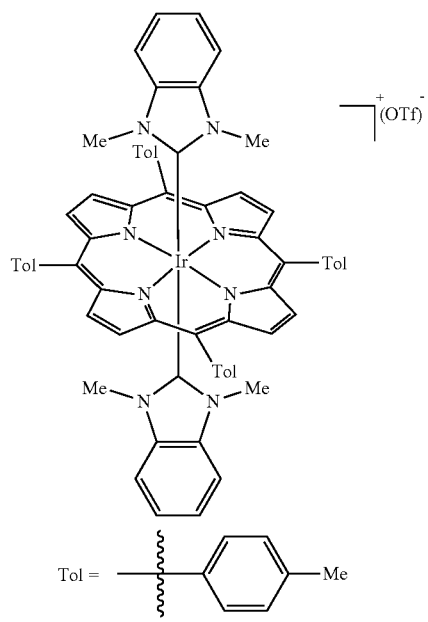
Complex 106
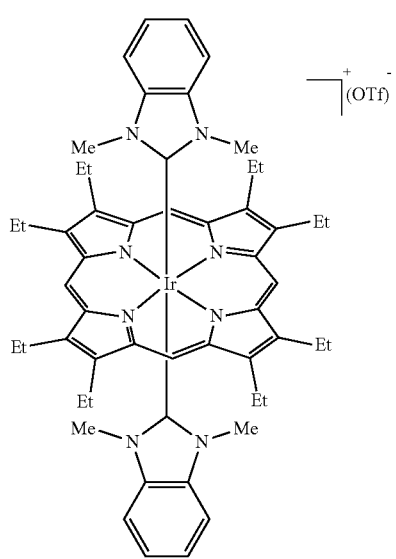
Complex 107
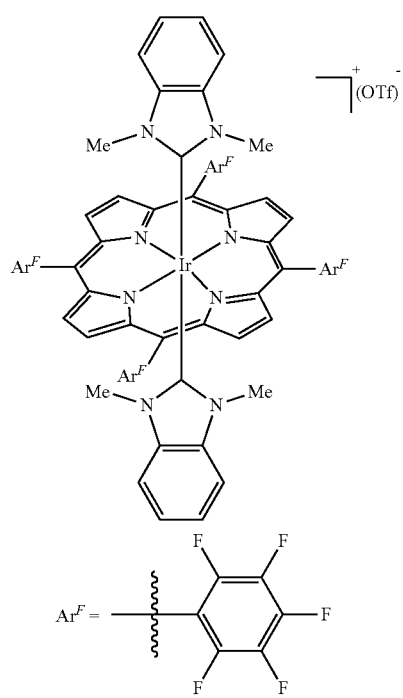
Complex 108
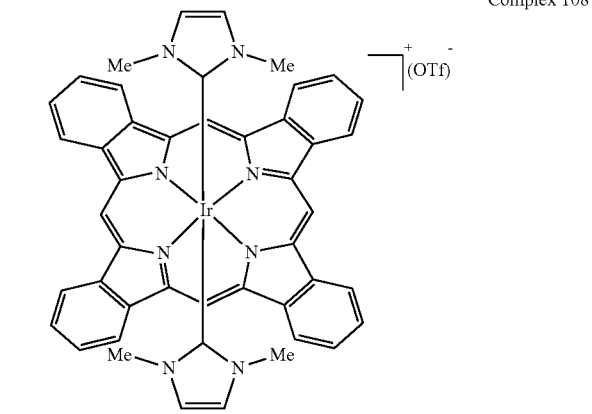
Complex 109
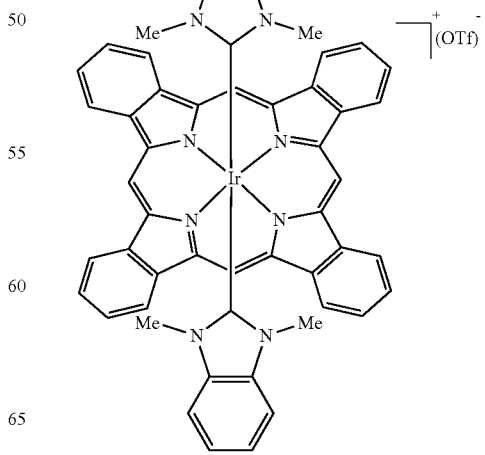

-continued

Complex 110

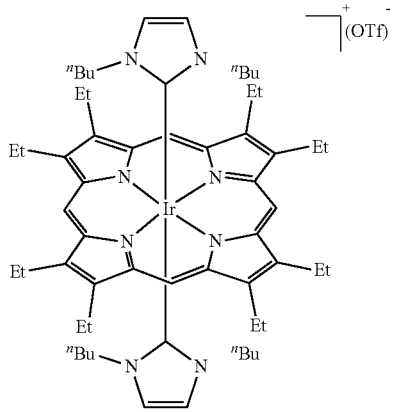

In one embodiment, provided herein is a method for cancer or tumor treatment and prevention resulting in induction of cell death, inhibition of cellular proliferation, inhibition of angiogenesis, or inhibition of in vivo tumor growth. In certain embodiment, the iridium (III) complexes exhibit potent cytotoxicity in the dark. In certain embodiment, the iridium (III) complexes has enhanced cytotoxicity upon light irradiation. In one embodiment, provided herein is a method comprising administering to a subject in need thereof a composition comprising an effective amount of a Ir(III)-NHC complex. In one embodiment, the Ir(III)-NHC complexes is a Iridium (III) complex described herein represented by the structural formulae of I, derivatives thereof; or a pharmaceutically acceptable salt, solvate, or hydrate thereof.

In another embodiment, provided herein is a method for detecting an effective amount of the Ir(III)-NHC complexes, depending on the fluorescence changes at proper wavelength. The Ir(III)-NHC complex is a Iridium (III) complex described herein can be represented by the structural formula of I, or an acceptable salt thereof.

The Ir(III)-NHC complexes are stable in air and aqueous solutions like phosphate-buffered saline (PBS) conditions. The anti-cancer active Ir(III)-NHC complexes is also accompanied with the release of highly fluorescent ligand. The Ir(III)-NHC complexes display similar anti-cancer or anti-tumor activity. They can be detected via the fluorescent ligand which makes them to be excellent bio-probes and for prevalent biological applications.

In certain embodiment, the iridium (III) complexes exhibit potent cytotoxicity in the dark. In certain embodiment, the iridium (III) complexes has enhanced cytotoxicity upon light irradiation.

4. BRIEF DESCRIPTION OF THE DRAWINGS

Figure 1:
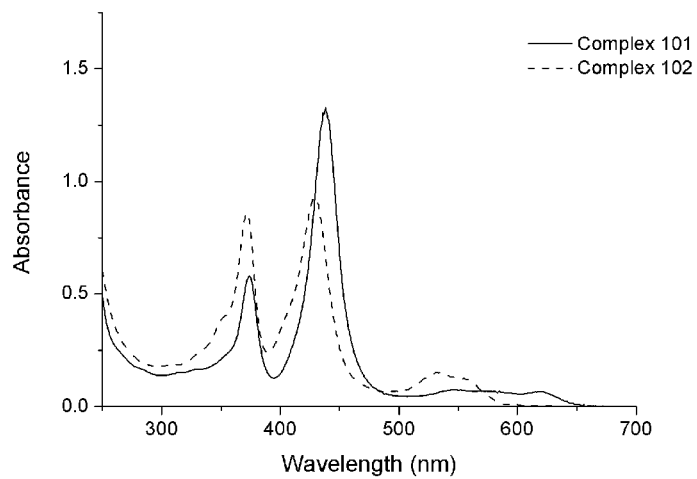
FIG. 1 shows UV-vis absorption spectra of Complex 101 and Complex 102 in $CHCl_3$.
Figure 2:
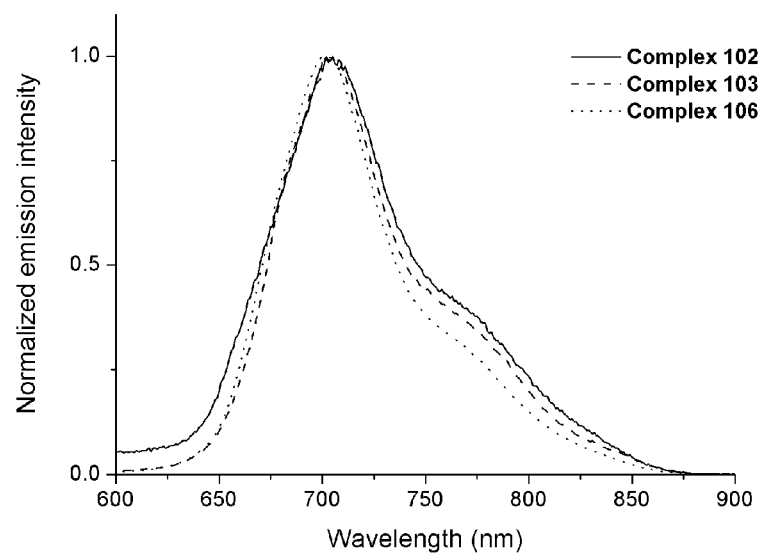
FIG. 2 shows Emission spectra of Complex 102, Complex 103 and Complex 106 in degassed $CHCl_3$.
Figure 3:
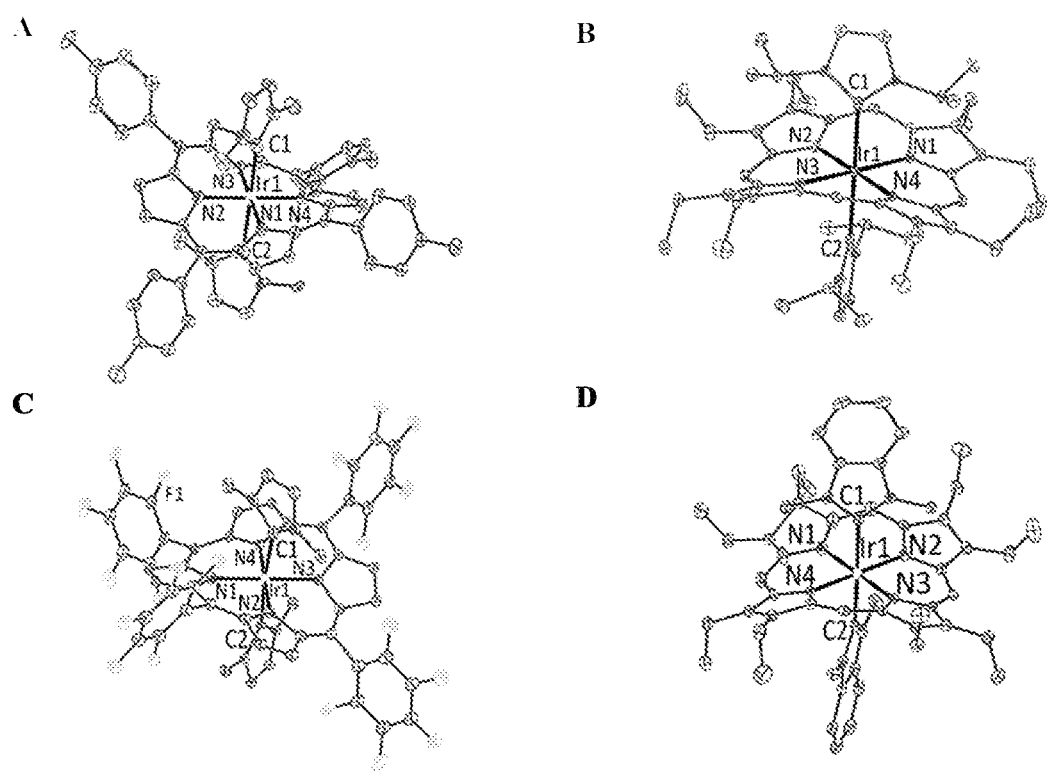
FIGS. 3A-3D shows perspective views of (A) Complex 101, (B) Complex 103, (C) Complex 103 and (D) Complex 104 at 30% probability of the thermal ellipsoid. Hydrogen atoms, co-crystallized solvent molecules and counter anions are omitted for clarity.
Figure 4:
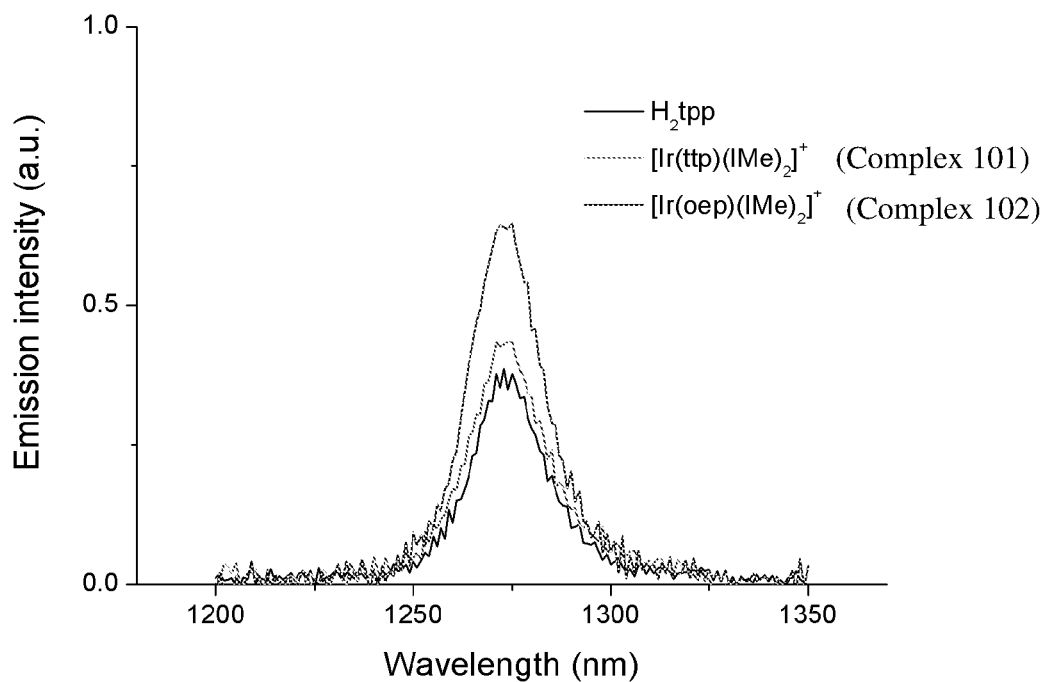

FIG. 4 shows Singlet oxygen emission spectra upon irradiating oxygen-saturated $CHCl_3$ solution of Complex 101 and Complex 102. By referencing to the $^1O_2$ emission intensity ($\lambda_{max}$=1270 nm) of $H_2$tpp ($\Phi$=so=0.55 in $CHCl_3$), the quantum yield of singlet oxygen generation ($\Phi_{so}$) of oxygen-saturated $CHCl_3$ solutions of Complex 101 and Complex 102 were found to be 0.64 and 0.88 respectively.

FIGS. 5A-5B show In vivo antitumor activity of Complex 102 in nude mouse model bearing NCI-H460 xenograft. (A) Tumor volume and (B) body weight of mice. Data are expressed as the mean±standard error; *p<0.05.

FIGS. 6A-6D show Confocal microscopy imaging of NCI-H460 cells treated with (A) Complex 102 (1 µM; $\lambda_{ex}$=555 nm, $\lambda_{em}$=650–750 nm) for 2 h and (B) ER-Tracker green ($\lambda_{ex}$=488 nm, $\lambda_{em}$=500–530 nm) for 15 min. (C) The merged images of (A) and (B). (D) Bright field. Scale bar: 20 µm.

FIGS. 7A-7C. (A) Generation of ROS examined by DCF fluorescence measurement in NCI-H460 cells treated with or without iridium(III) porphyrin complexes (1 µM) for 2 h with or without irradiation by visible light. (B) Confocal microscopy imaging of ROS generation in cells incubated with complex 102 with or without irradiation by visible light. Scale bar: 20 µm. (C) ESI-MS/MS spectra of the triply charged disulfide-bridged peptide (m/z 421.8638; top) and oxidized peptides (m/z 427.1954; middle, ink 433.1978; bottom). Fragments with blue labels indicate sites of disulfide bond formation, and red labels represent oxidative modification sites.

Figure 8:
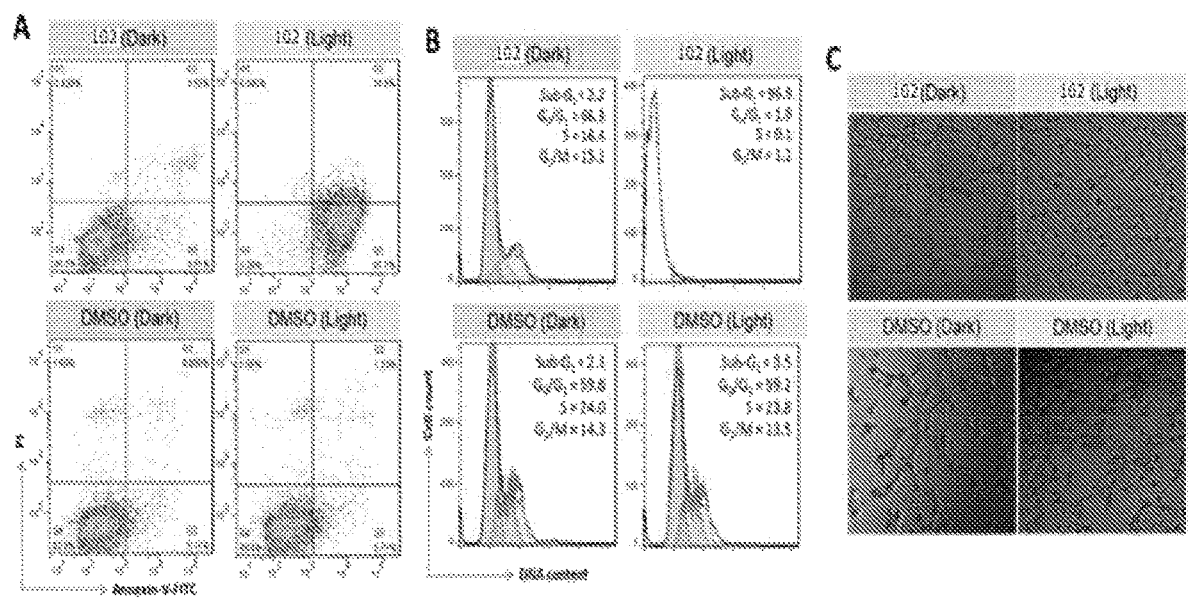

FIGS. 8A-8C. Anticancer properties of Complex 102 (0.1 µM) upon visible light irradiation. (A) Apoptosis/necrosis in NCI-H460 cells as examined by flow cytometry of annexin-V-FITC/propidium iodide-stained cells. (B) Cell cycle progression in NCI-H460 cells as examined by flow cytometry. (C) Inhibition of angiogenesis of MS-1 endothelial cells.

FIGS. 9A-9D. In vivo antitumor effects of Complex 102 in nude mouse model bearing NCI-H460 lung cancer xenografts. (A) Tumor volume. (B) Body weight of mice. (C) Tumor weight after the experiment. Red arrows indicate the injection of the mice with Complex 102 together with irradiation on day 0 and day 7. (D) Photo of tumors of each group after treatment for 15 days. Data are expressed as the mean±standard error; **p<0.01.

Figure 10:
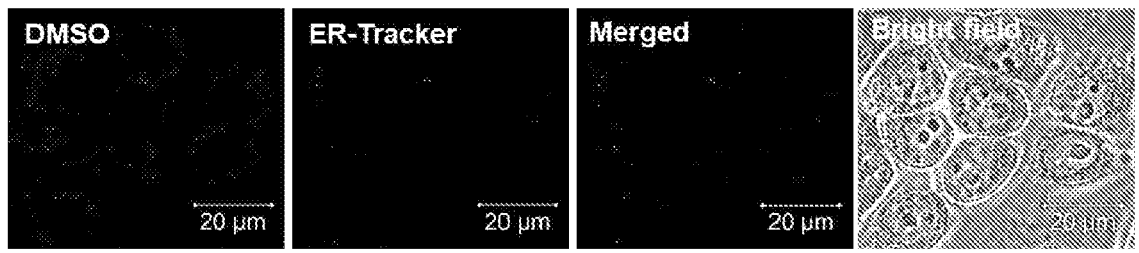

FIG. 10. Confocal microscopy imaging of NCI-H460 cells treated with DMSO vehicle ($\lambda$=555 nm, $\lambda_{em}$,=650–750 nm) for 2 h. Cells were co-stained with ER-Tracker green ($\lambda$=488 nm, $\lambda_{em}$=500–530 nm) for 15 min. Scale bar: 20 µm.

FIGS. 11A-11B. Confocal microscopy imaging of NCI-H460 cells treated with (A) complex 102 (1 µM; $\lambda_{ex}$=555 nm, $\lambda_{em}$=650–750 nm) or (B) DMSO vehicle for 2 h. Cells were co-stained with Mito-Tracker green ($\lambda_{ex}$=488 nm, $\lambda_{em}$=500–530 nm) for 15 min. Scale bar: 20 µm.

FIG. 12A-12G. Plots of cell viability of NCI-H460 lung cancer cells upon 72 h treatment with the iridium(III) porphyrin complexes and cis-platin in dark or under light irradiation (2.8 mW $cm^{-2}$ for 1 h).

Figure 13:
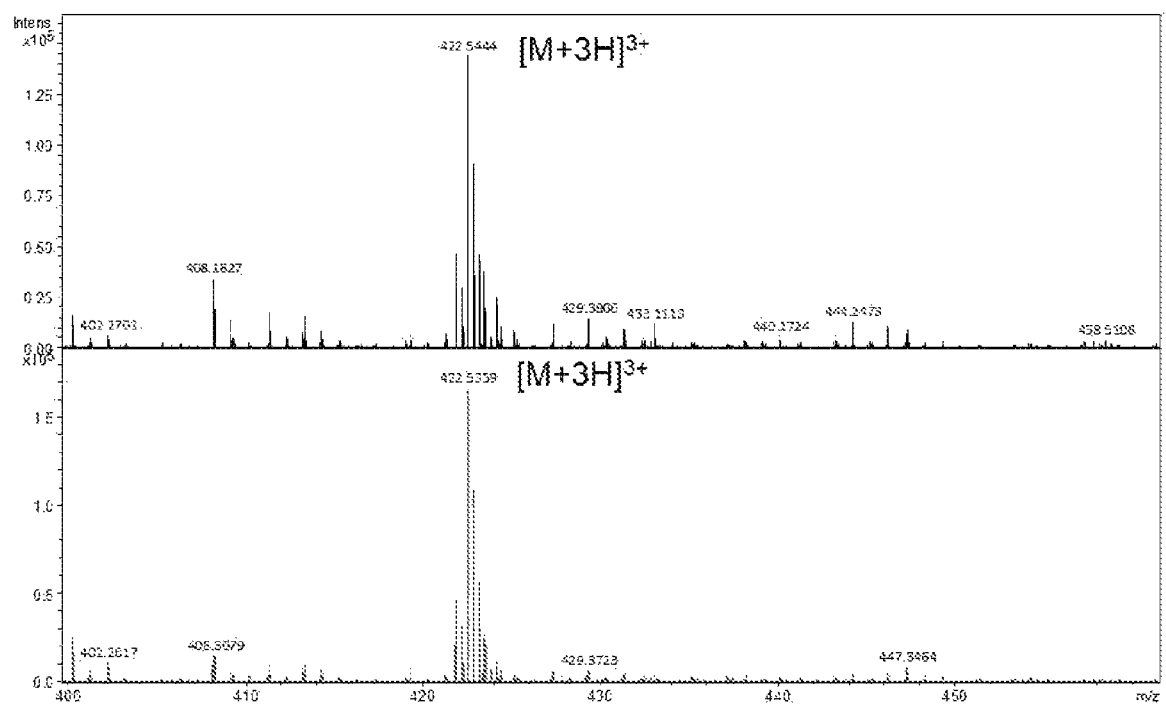

FIG. 13. ESI-MS spectra of triply charged peptide (RIMKCPGCWTA, 20 µM) at m/z 422.54 after incubation in dark (upper) or upon light irradiation (lower) for 1 h.

Figure 14:
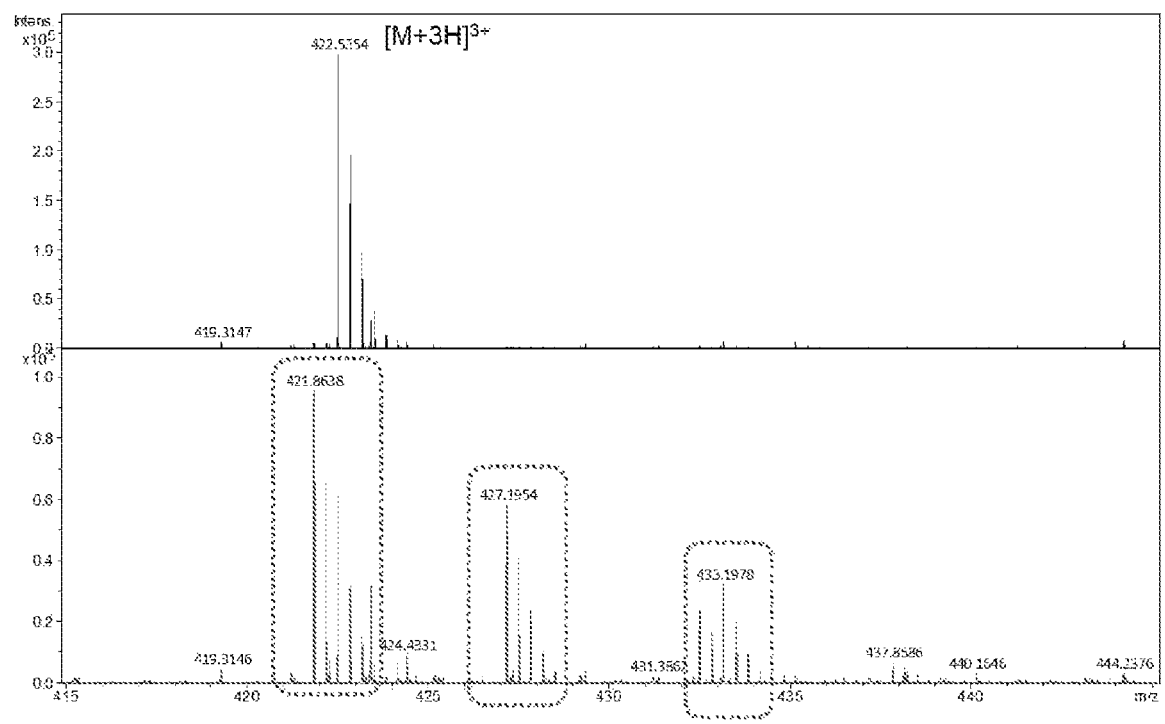

FIG. 14. ESI-MS spectra of triply charged peptide (RIMKCPGCWTA, 20 µM) with complex 102 (10 µM) after incubation in dark (upper) or upon light irradiation (lower) for 1 h. The red dotted lines indicate the oxidative modification of the peptide.

Figure 15:
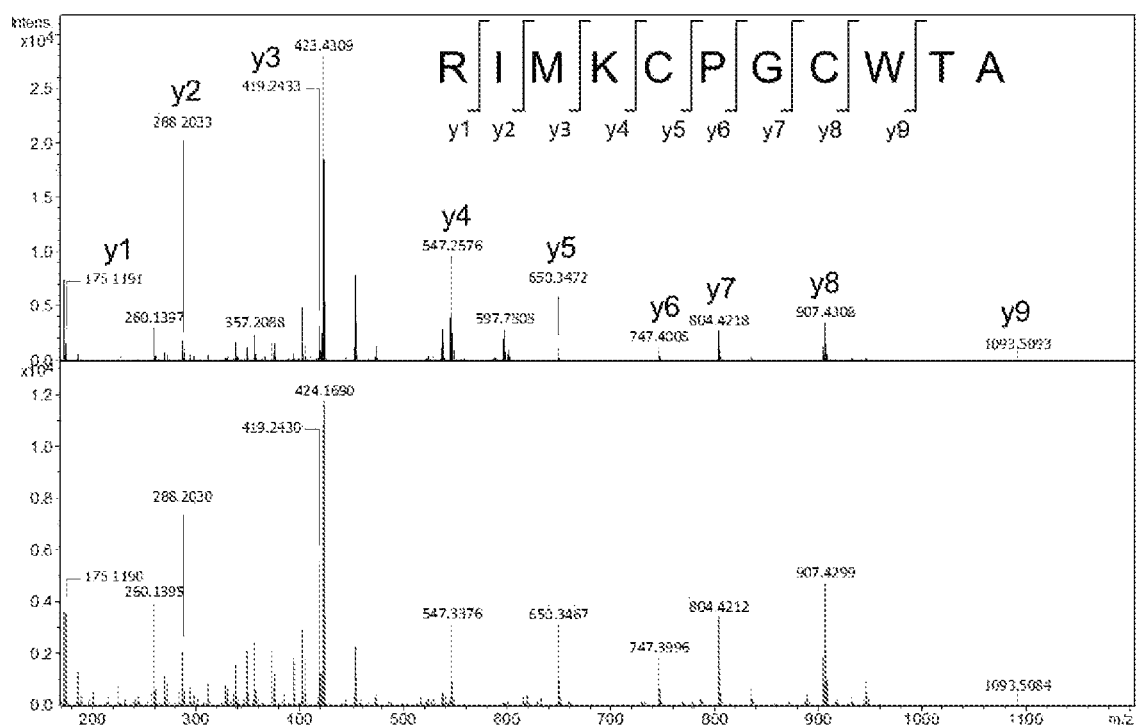

FIG. 15. MS/MS spectra of triply charged peptide (RIMKCPGCWTA, 20 µM) at m/z 422.54 after incubation in dark (upper) or upon light irradiation (lower) for 1 h.

Figure 16:
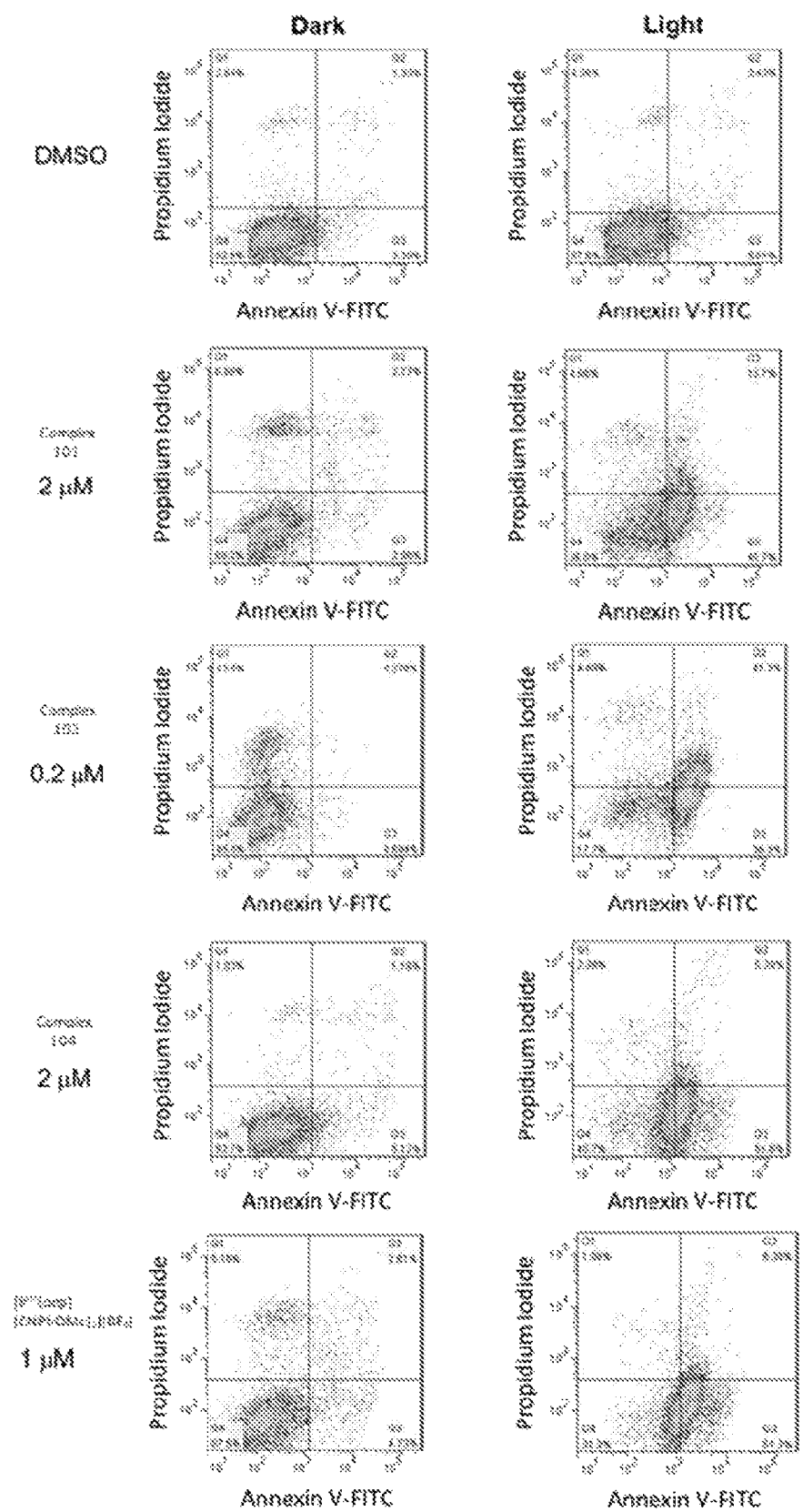

FIG. 16. Flow cytometric analysis of Annexin V/PI double stained NCI-H460 cells treatment with vehicle control, complex 101, 103, 104, [Ir$^{III}$(ope)(CNPhOMe)$_2$](BF$_4$) (14 h) in the absence or presence of light irradiation (2.8 mW cm$^{-2}$, 1 h).

Figure 17:
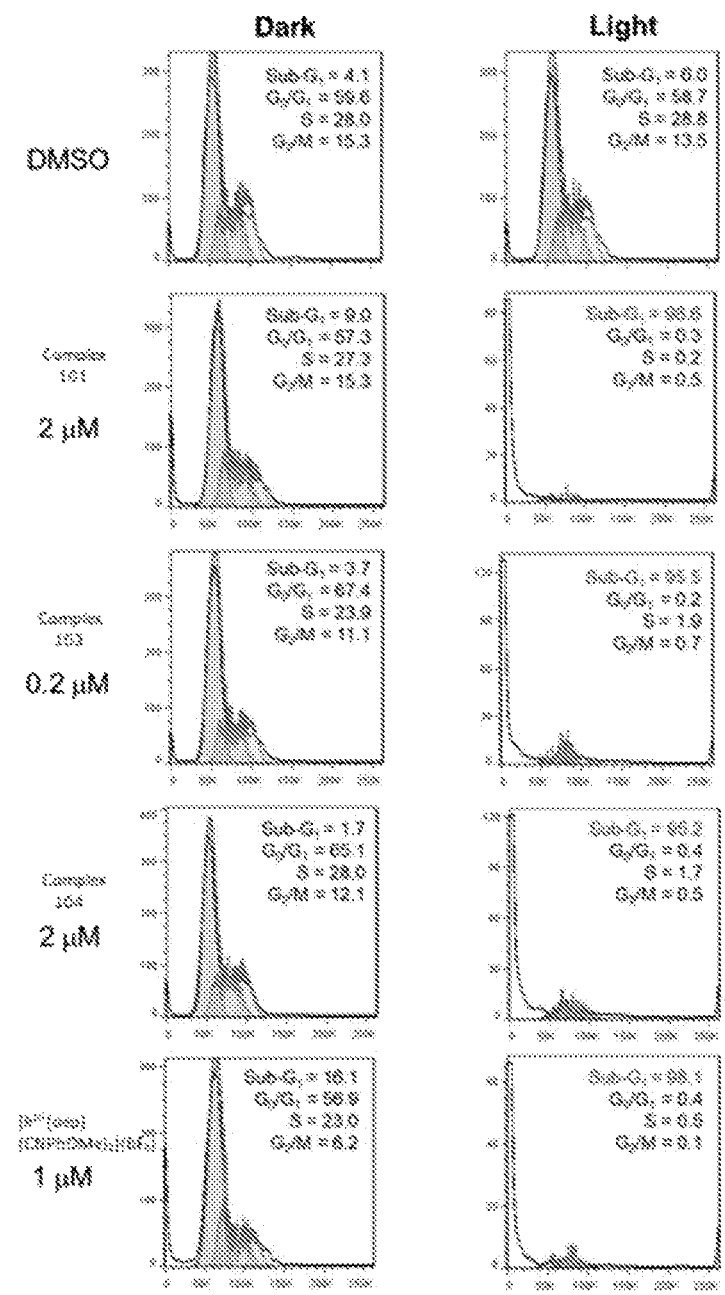

FIG. 17. Cell cycle progression analysis of DAPI-stained NCI-H460 cells treatment with vehicle control, complex 101, 103, 104 and [Ir$^{III}$(oep)(CNPhOMe)$_2$](BF$_4$) (14 h) in the absence or presence of light irradiation (2.8 mW cm$^{-2}$, 1 h) by flow cytometry.

Figure 18:
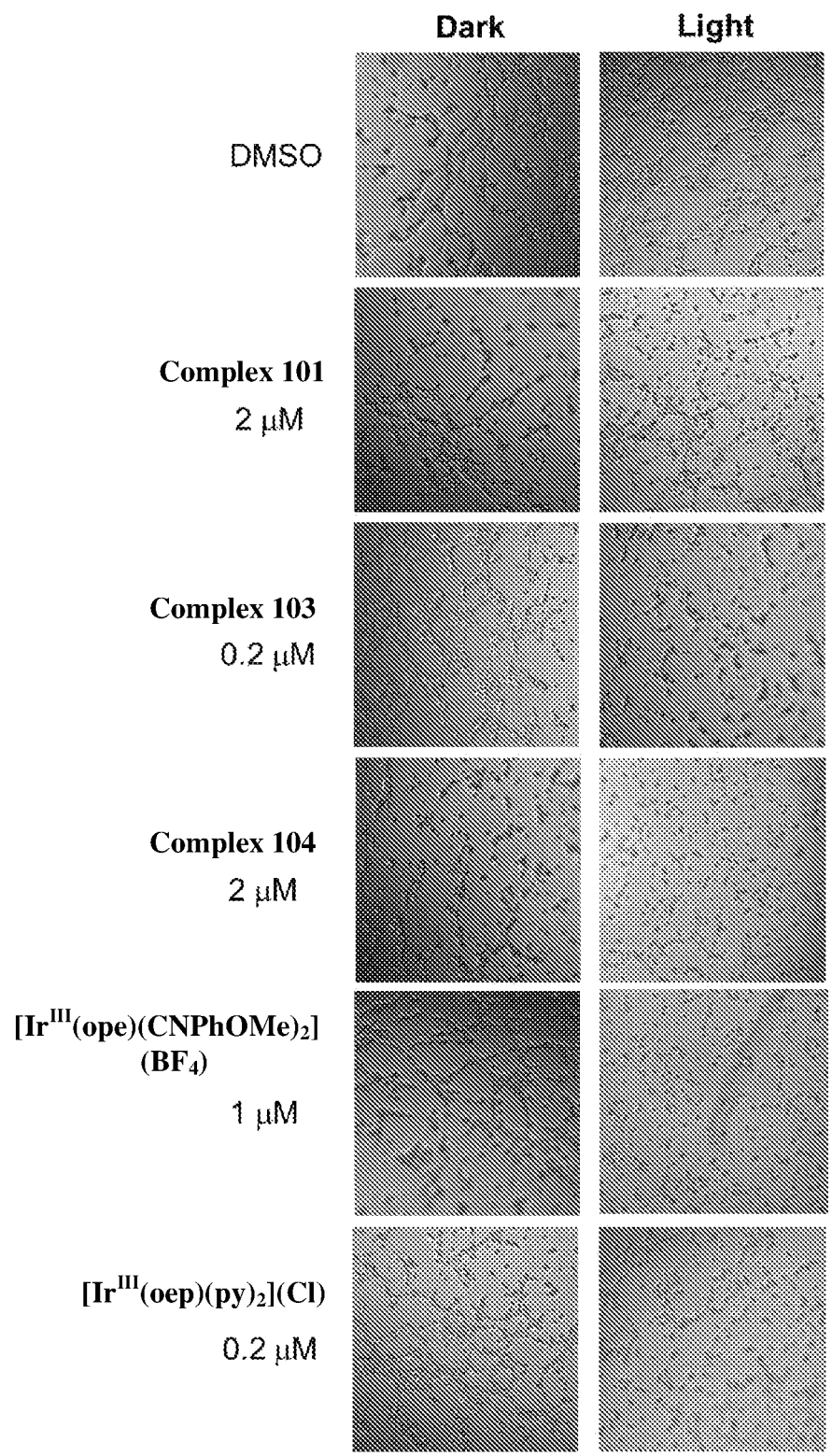

FIG. 18. Microscopic examination of the cellular tube formation of MS-1 endothelial cells after treatment with vehicle control, complex 101, 103, 104, [Ir$^{III}$(oep)(CNPhOMe)$_2$](BF$_4$) and [Ir$^{III}$(oep)(py)$_2$](Cl) (1 h) in the absence or presence of light irradiation (2.8 mW cm$^{-2}$, 1 h).

5. DETAILED DESCRIPTION

Provided herein is a new series of dual cytotoxic and anti-angiogenic Iridium (III) complexes with N-heterocylic carbene (NHC). The introduction of NHC ligand, which is a strong σ-donor, also renders the complexes strong luminescence in aqueous solution and live cells, and hence their subcellular localization in endoplasmic reticulum (ER) can be identified by fluorescence microscopy. With their accumulation in ER, they are found to induce ER stress and subsequent apoptotic cell death, accounting for their potent cytotoxicity toward cancer cells. The present invention discloses that luminescent Ir$^{III}$-porphyrin complexes with axially coordinating N-heterocyclic carbene (NHC) ligands with strong singlet oxygen generation capacity exhibit potent antitumor activities under dark and light irradiation conditions.

5.1 Ir(III) Complexes, Synthesis and Use

Disclosed are iridium (III) [Ir(III)] complexes containing N-heterocyclic carbene ligand (NHC), their synthesis, composition comprising iridium (III) [Ir(III)] complexes containing N-heterocyclic carbene ligand (NHC), methods of treating and preventing cancer or tumor in a subject, and a method of detecting the Ir(III) complex. Disclosed herein is a method of treating or preventing cancer/tumor comprising administering a pharmaceutical composition comprising at least one of the Ir(III)-NHC complexes in an effective amount for anti-cancer or anti-tumor activity. In certain embodiments, anti-cancer or anti-tumor activities includes, but are not limited to, the induction of cell death, inhibition of cellular proliferation, inhibition of angiogenesis, and inhibition of in vivo tumor growth. Provided herein is a method of detecting the Ir(III)-NHC complexes. In an embodiment, a signal is detected depending on fluorescence changes at proper wavelength. As provided herein, in one embodiment, Ir(III)-NHC complexes refer to a molecule of a Iridium (III) ion connected to a N-heterocyclic carbene ligand. In one embodiment, Iridium (III) [Ir(III)] complexes containing N-heterocyclic carbene ligand (NHC) is represented by structural formula I, derivatives thereof; or a pharmaceutically acceptable salt, solvate, or hydrate thereof.

"Halogen" means fluorine (F), chlorine (Cl), bromine (Br) and iodine (I).

"Alkyl" refers to a radical of a straight-chain or branched saturated hydrocarbon group having from 1 to 20, preferably 1 to 10, preferably 1 to 6 carbon atoms. In some embodiments, $C_{1-4}$ alkyl is particularly preferred. Examples of alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-6}$ alkyl (e.g., —CH$_3$). In certain embodiments, the alkyl group is substituted $C_{1-6}$ alkyl.

"Cycloalkyl" refers to a radical of a non-aromatic cyclic hydrocarbon group having from 3 to 20, preferably 3 to 10, preferably 3 to 7 ring carbon atoms and zero heteroatoms. In some embodiments, $C_{3-6}$ cycloalkyl is especially preferred, and $C_{5-6}$ cycloalkyl is more preferred. Cycloalkyl also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Exemplary cycloalkyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), and the like. Unless otherwise specified, each instance of a cycloalkyl group is independently optionally substituted, i.e., unsubstituted (an "unsubstituted cycloalkyl") or substituted (a "substituted cycloalkyl") with one or more substituents. In certain embodiments, the cycloalkyl group is unsubstituted $C_{3-7}$ cycloalkyl. In certain embodiments, the cycloalkyl group is a substituted $C_{3-7}$ cycloalkyl.

"Aryl" refers to a radical of a monocyclic or polycyclic (e.g., bicyclic) 4n+2 aromatic ring system (e.g., having 6, 10, 14, 18, 22πelectrons shared in a cyclic array) having 6-22, preferably 6-18, preferably 6-14, preferaby 6-10 ring carbon atoms and zero heteroatoms. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). Aryl also includes ring systems wherein the aryl ring, as defined above, is fused with one or more cycloalkyl, or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-10}$ aryl. In certain embodiments, the aryl group is substituted $C_{6-10}$ aryl.

"Acyl" refers to a radical of R—C(O)—, wherein R is as defined above for alkyl.

"Alkoxy" refers to the group —OR wherein R is as defined above for alkyl.

In some embodiments, $C_{1-4}$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"Acyloxy" refers to a radical of R—C(O)O—, wherein R is as defined above for alkyl.

"Amino" refers to a radical of RR'N—, wherein R and R' are as defined above for alkyl.

"Acylamino" refers to a radical of R—C(O)—NR'—, wherein R and R' are as defined above for alkyl.

"Aralkyl" refers to a radical of RR'-, wherein R is as defined above for alkyl, and R' is as defined above for aryl.

As used herein, the phrase "acceptable salt," as used herein, includes salts formed from the charged Ir(III)-NHC complex and counter-anion(s).

As used herein, the phrase "counter-anion" refers to an ion associated with a positively charged Ir(III)-NHC complex. Non-limiting examples of counter-ions include halogens such as fluoride ($F^-$), chloride ($Cl^-$), bromide ($Br^-$), iodide ($I^-$); sulfate ($SO_4^{2-}$); phosphate ($PO_4^{3-}$); trifluoromethanesulfonate (triflate, $^-OTf$ or $CF_3SO_3^-$); acetate ($^-OAc$); nitrate ($NO_3^-$); perchlorate ($ClO_4^-$); hexafluorophosphate ($PF_6^-$), hexafluoroacetylacetonate ($[CF_3C(O)CHC(O)CF_3]^-$), tetrafluoroborate ($BF_4^-$), tetraphenylborate ($BPh_4^-$) and hexafluoroantimonate ($SbF_6$).

In one embodiment, the disclosure relates to the synthesis of novel Iridium (III) [Ir(III)] bearing N-heterocyclic carbene ligand.

In another embodiment, the disclosure relates to a pharmaceutical composition for cancer treatment by inhibition of the proliferation of cancer cells in vitro comprising an effective amount of one or more of the Ir(III)-NHC complexes.

In another embodiment, the disclosure relates to a pharmaceutical composition for cancer treatment by the inhibition of tumor growth in vivo comprising an effective amount of one or more of the Ir(III)-NHC complexes.

In another embodiment, the disclosure relates to fluorescent detecting compounds, and the application in cellular imaging, comprising an effective amount of a Ir(III)-NHC complex.

The Ir(III)-NHC complexes of this disclosure can be represented by one or more of structural formula I, derivatives thereof; or a pharmaceutically acceptable salt, solvate, or hydrate thereof.

In one embodiment, the disclosure relates to a pharmaceutical composition for treating or preventing cancer/tumor. In certain embodiments, the treatment and prevention comprises induction of cell death, inhibition of cellular proliferation, inhibition of angiogenesis, and the inhibition of tumor growth in vivo. In one embodiment, the method comprises administering an effective amount of the Ir(III)-NHC complexes to a subject.

In one embodiment, the method comprises detecting the Ir(III) complex in a subject comprising administering an effective amount of the Ir(III)-NHC complexes. In one embodiment, the Ir(III) complex is detected by fluorescence changes at proper wavelength. The Ir(III)-NHC complex has a formula I, derivatives thereof; or a pharmaceutically acceptable salt, solvate, or hydrate thereof.

5.2 Human Treatment

5.2.1 Formulations

The Iridium (III) complexes provided herein can be administered to a patient in the conventional form of preparations, such as injections and suspensions. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the Iridium (III) complexes provided herein in the pharmaceutical composition may be at a level that will exercise the desired effect.

In another embodiment, provided herein are compositions comprising an effective amount of Iridium (III) complexes provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing the Iridium (III) complexes provided herein with a suitable carrier or diluent and filling the proper amount of the mixture in capsules.

5.3 Method of Use

The composition of the present disclosure may be applied directly to the tumor, and/or applied systemically to the body of the subject such that at least some of the composition is able to travel to the tumor (e.g., via the blood) such that light can be applied to the tumor (or portion thereof), to treat the tumor. The composition can include, for example, an anti-angiogenesis drug, an anti-inflammatory drug, a radioactive species, an anticancer drug and/or a chemotherapy drug, and light may be applied to the tumor to cause release. Such application may be targeted, e.g., by applying light directly to the tumor (or at least a portion thereof); thus, release elsewhere within the subject may be minimized by not applying light to other places. In such a fashion, the effectiveness of the therapeutics may be enhanced, controlled or localized at or near the tumor by applying light directly to the tumor (or portion thereof), or at least proximate the tumor. In some cases, more than one composition may be present.

Other portions of a subject may also be treated in various embodiments. For instance, the composition may be applied directly to a specific location within the subject, or applied systemically to the subject such that at least some of the composition is able to travel to a location where light is to be applied. For instance, the composition may be applied to the skin (or to the blood) and light applied to a portion of the skin to enhance the effectiveness of the therapeutics.

Solid tumor cancers that can be treated by the methods provided herein include, but are not limited to, sarcomas, carcinomas, and lymphomas. In specific embodiments, cancers that can be treated in accordance with the methods described include, but are not limited to, cancer of the breast, liver, neuroblastoma, head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of Iridium (III) complexes as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of Iridium (III) complexes as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of Iridium (III) complexes as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of Iridium (III) complexes, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of Iridium (III) complexes, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of Iridium (III) complexes, as assessed by methods well known in the art, e.g., PET scan.

5.4 Patient Population

In some embodiments, a subject treated for cancer in accordance with the methods provided herein is a human who has or is diagnosed with cancer. In other embodiments, a subject treated for cancer in accordance with the methods provided herein is a human predisposed or susceptible to cancer. In some embodiments, a subject treated for cancer in accordance with the methods provided herein is a human at risk of developing cancer.

In one embodiment, a subject treated for cancer in accordance with the methods provided herein is a human infant. In another embodiment, a subject treated for cancer in accordance with the methods provided herein is a human toddler. In another embodiment, a subject treated for cancer in accordance with the methods provided herein is a human child. In another embodiment, a subject treated for cancer in accordance with the methods provided herein is a human adult. In another embodiment, a subject treated for cancer in accordance with the methods provided herein is a middle-aged human. In another embodiment, a subject treated for cancer in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer in accordance with the methods provided herein is a human that is 18 years old or older. In a particular embodiment, a subject treated for cancer in accordance with the methods provided herein is a human child that is between the age of 1 year old to 18 years old. In a certain embodiment, a subject treated for cancer in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for cancer in accordance with the methods provided herein is administered Iridium (III) complexes or a pharmaceutical composition thereof, or a combination therapy before any adverse effects or intolerance to therapies other than the Iridium (III) complexes develops. In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer accordance with the methods provided herein is a human that has proven refractory to therapies other than treatment with Iridium (III) complexes, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring tumors despite treatment with existing therapies.

5.5 Dosage

In one aspect, a method for treating cancer presented herein involves the administration of a unit dosage of Iridium (III) complexes or a pharmaceutical composition thereof. The dosage may be administered as often as determined effective (e.g., once, twice or three times per day, every other day, once or twice per week, biweekly or monthly). In certain embodiments, a method for treating cancer presented herein involves the administration to a subject in need thereof of a unit dose of Iridium (III) complexes that can be determined by one skilled in the art.

In some embodiments, a unit dose of Iridium (III) complexes or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

In certain embodiment, the iridium (III) complexes exhibit potent cytotoxicity in the dark. In certain embodiment, the iridium (III) complexes has enhanced cytotoxicity upon light irradiation.

In certain embodiments, the light irradiation uses light with certain wavelength in the visible light spectrum, i.e., about 390 to about 700 nm. However, in some instances, infrared light (e.g., about 650 nm to about 1350 nm, or about 700 nm to about 1200 nm, etc.) may be used.

As non-limiting examples, light irradiation may use light having a wavelength of at least about 300 nm-350 nm, at least about 350 nm-400 nm, at least about 400 nm-450 nm, at least about 450 nm-500 nm, at least about 500 nm-550 nm, at least about 550 nm-600 nm, at least about 600 nm-650 nm, at least about 650 nm-700 nm, at least about 750 nm-800 nm, at least about 800 nm-850 nm, at least about 850 nm-900 nm, at least about 900 nm-950 nm, at least about 950 nm-1000 nm, at least about 1000 nm-1100 nm, at least about 1100 nm-1200 nm. The light may be monochromatic light (e.g., laser or coherent light), or the light may be nonmonochromatic or noncoherent in some embodiments. The light may have any suitable frequency, e.g., including the frequencies discussed herein.

5.6 Combination Therapy

Presented herein are combination therapies for the treatment of cancer which involve the administration of Iridium (III) complexes in combination with one or more additional therapies to a subject in need thereof. In a specific embodiment, presented herein are combination therapies for the treatment of cancer which involve the administration of an effective amount of Iridium (III) complexes in combination with an effective amount of another therapy to a subject in need thereof.

As used herein, the term "in combination," refers, in the context of the administration of Iridium (III) complexes, to the administration of Iridium (III) complexes prior to, concurrently with, or subsequent to the administration of one or more additional therapies (e.g., agents, surgery, or radiation) for use in treating cancer.

The use of the term "in combination" does not restrict the order in which Iridium (III) complexes and one or more additional therapies are administered to a subject. In specific embodiments, the interval of time between the administration of Iridium (III) complexes and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, Iridium (III) complexes and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering Iridium (III) complexes daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, Iridium (III) complexes and one or more additional therapies are cyclically administered to a subject. Cycling therapy involves the administration of Iridium (III) complexes for a period of time, followed by the administration of one or more additional therapies for a period of time, and repeating this sequential administration. In certain embodiments, cycling therapy may also include a period of rest where Iridium (III) complexes or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer provided herein comprise administering Iridium (III) complexes as a single agent for a period of time prior to administering the Iridium (III) complexes in combination with an additional therapy. In certain embodiments, the methods for treating cancer provided herein comprise administering an additional therapy alone for a period of time prior to administering Iridium (III) complexes in combination with the additional therapy.

In some embodiments, the administration of Iridium (III) complexes and one or more additional therapies in accordance with the methods presented herein have an additive effect relative the administration of Iridium (III) complexes or said one or more additional therapies alone. In some embodiments, the administration of Iridium (III) complexes and one or more additional therapies in accordance with the methods presented herein have a synergistic effect relative to the administration of the Compound or said one or more additional therapies alone.

As used herein, the term "synergistic," refers to the effect of the administration of Iridium (III) complexes in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of Iridium (III) complexes or an additional therapy and/or less frequent administration of Iridium (III) complexes or an additional therapy to a subject. In certain embodiments, the ability to utilize lower dosages of Iridium (III) complexes or of an additional therapy and/or to administer Iridium (III) complexes or said additional therapy less frequently reduces the toxicity associated with the administration of Iridium (III) complexes or of said additional therapy, respectively, to a subject without reducing the efficacy of Iridium (III) complexes or of said additional therapy, respectively, in the treatment of cancer. In some embodiments, a synergistic effect results in improved efficacy of Iridium (III) complexes and each of said additional therapies in treating cancer. In some embodiments, a synergistic effect of a combination of Iridium (III) complexes and one or more additional therapies avoids or reduces adverse or unwanted side effects associated with the use of any single therapy.

The combination of Iridium (III) complexes and one or more additional therapies can be administered to a subject in the same pharmaceutical composition. Alternatively, Iridium (III) complexes and one or more additional therapies can be administered concurrently to a subject in separate pharmaceutical compositions. Iridium (III) complexes and one or more additional therapies can be administered sequentially to a subject in separate pharmaceutical compositions. Iridium (III) complexes and one or more additional therapies may also be administered to a subject by the same or different routes of administration.

The combination therapies provided herein involve administering to a subject to in need thereof Iridium (III) complexes in combination with conventional, or known, therapies for treating cancer. Other therapies for cancer or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with or a condition associated therewith.

Specific examples of anti-cancer agents that may be used in combination with Iridium (III) complexes include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with Iridium (III) complexes include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with Iridium (III) complexes include microtubule disasssembly blocker, antimetabolite, topisomerase inhibitor, and DNA crosslinker or damaging agent. Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide);

anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of other therapies that may be administered to a subject in combination with Iridium (III) complexes include:

(1) a statin such as lovostatin (e.g., branded/marketed as MEVACOR®);

(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;

(3) a farnesyltransferase inhibitor agent such as tipifarnib;
(4) an antifibrotic agent such as pirfenidone;
(5) a pegylated interferon such as PEG-interferon alfa-2b;
(6) a CNS stimulant such as methylphenidate (branded/marketed as RITALIN®);
(7) a HER-2 antagonist such as anti-HER-2 antibody (e.g., trastuzumab) and kinase inhibitor (e.g., lapatinib);

(8) an IGF-1 antagonist such as an anti-IGF-1 antibody (e.g., AVE1642 and IMC-A11) or an IGF-1 kinase inhibitor;

(9) EGFR/HER-1 antagonist such as an anti-EGFR antibody (e.g., cetuximab, panitumamab) or EGFR kinase inhibitor (e.g., erlotinib; gefitinib);

(10) SRC antagonist such as bosutinib;

(11) cyclin dependent kinase (CDK) inhibitor such as seliciclib;

(12) Janus kinase 2 inhibitor such as lestaurtinib;

(13) proteasome inhibitor such as bortezomib;

(14) phosphodiesterase inhibitor such as anagrelide;

(15) inosine monophosphate dehydrogenase inhibitor such as tiazofurine;

(16) lipoxygenase inhibitor such as masoprocol;

(17) endothelin antagonist;

(18) retinoid receptor antagonist such as tretinoin or alitretinoin;

(19) immune modulator such as lenalidomide, pomalidomide, or thalidomide;

(20) kinase (e.g., tyrosine kinase) inhibitor such as imatinib, dasatinib, erlotinib, nilotinib, gefitinib, sorafenib, sunitinib, lapatinib, or TG100801;

(21) non-steroidal anti-inflammatory agent such as celecoxib (branded/marketed as CELEBREX®);

(22) human granulocyte colony-stimulating factor (G-CSF) such as filgrastim (branded/marketed as NEUPOGEN®);

(23) folinic acid or leucovorin calcium;

(24) integrin antagonist such as an integrin $\alpha 5\beta 1$-antagonist (e.g., JSM6427);

(25) nuclear factor kappa beta (NF-$\kappa\beta$) antagonist such as OT-551, which is also an anti-oxidant;

(26) hedgehog inhibitor such as CUR61414, cyclopamine, GDC-0449, and anti-hedgehog antibody;

(27) histone deacetylase (HDAC) inhibitor such as SAHA (also known as vorinostat (branded/marketed as ZOLINZA)), PCI-24781, SB939, CHR-3996, CRA-024781, ITF2357, JNJ-26481585, or PCI-24781;

(28) retinoid such as isotretinoin (e.g., branded/marketed as ACCUTANE®);

(29) hepatocyte growth factor/scatter factor (HGF/SF) antagonist such as HGF/SF monoclonal antibody (e.g., AMG 102);

(30) synthetic chemical such as antineoplaston;

(31) anti-diabetic such as rosaiglitazone (e.g., branded/marketed as AVANDIA®);

(32) antimalarial and amebicidal drug such as chloroquine (e.g., branded/marketed as ARALEN®);

(33) synthetic bradykinin such as RMP-7;

(34) platelet-derived growth factor receptor inhibitor such as SU-101;

(35) receptor tyrosine kinase inhibitorsof Flk-1/KDR/VEGFR2, FGFR1 and PDGFR beta such as SU5416 and SU6668;

(36) anti-inflammatory agent such as sulfasalazine (e.g., branded/marketed as AZULFIDINE®); and

(37) TGF-beta antisense therapy.

6 EXAMPLES
Example 6.1: Preparation and Characterization of the NHC Complexes
The following examples illustrate the synthesis and characterization of the Iridium (III) complexes.
Examples of the Ir(III)-NHC Complexes
Complex 101
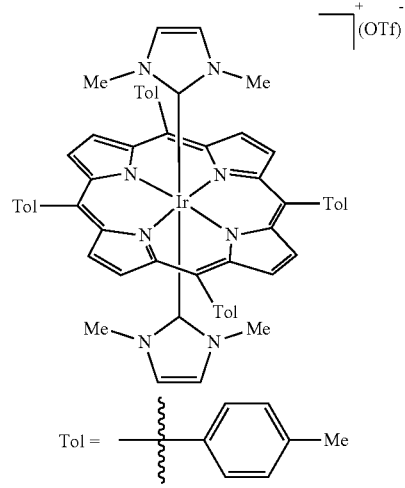
Complex 102
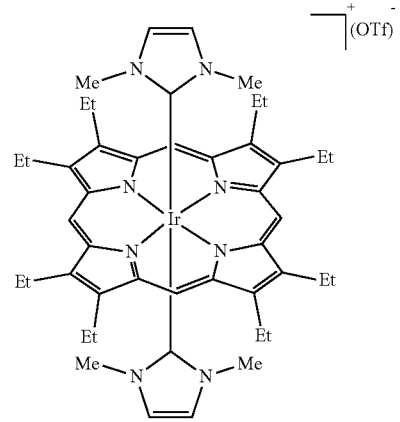
Complex 103
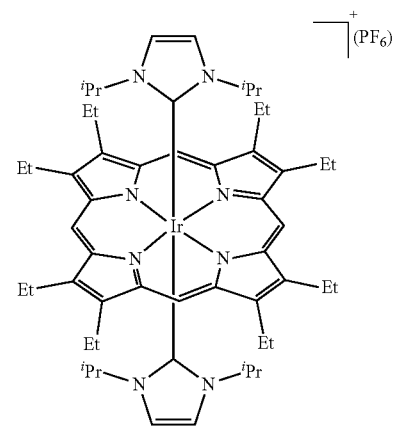
Complex 104
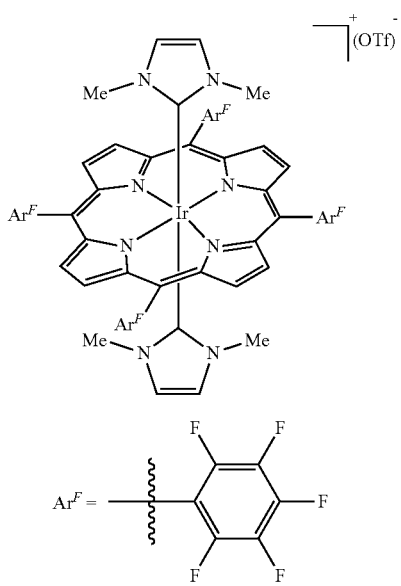
Complex 105
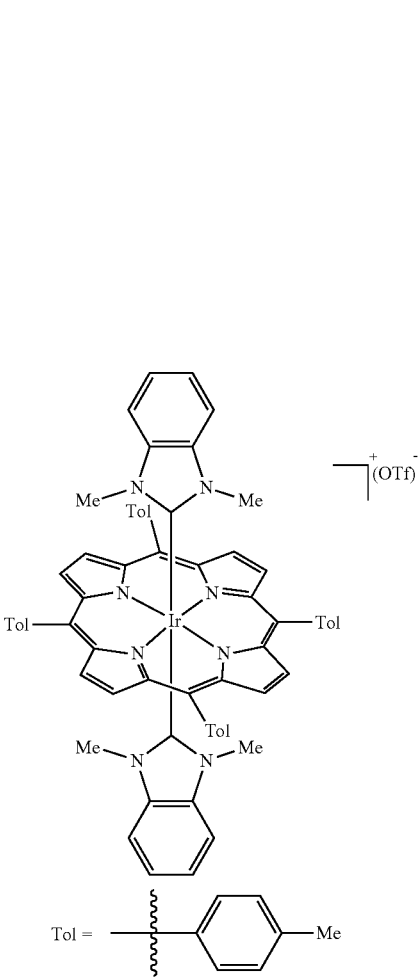

-continued
Complex 106
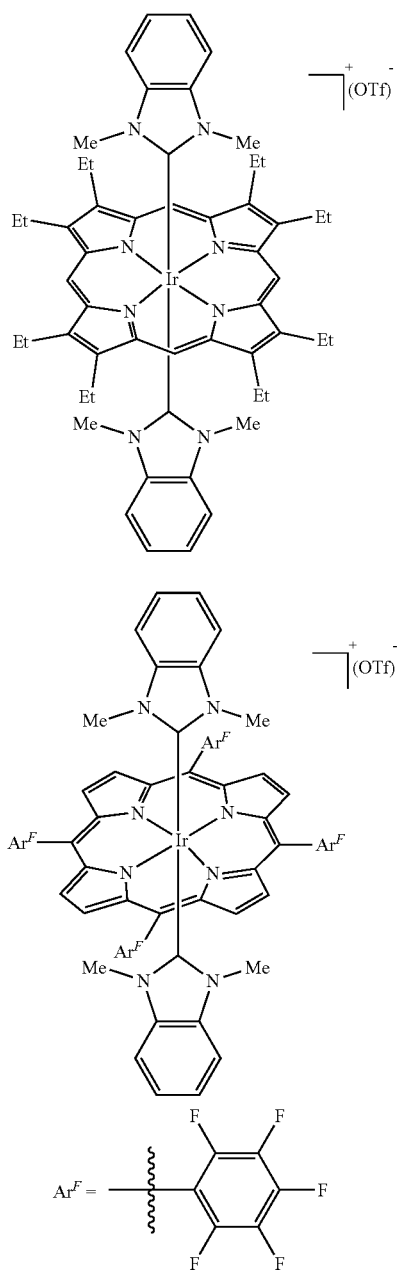
Complex 107
Complex 108
-continued
Complex 109
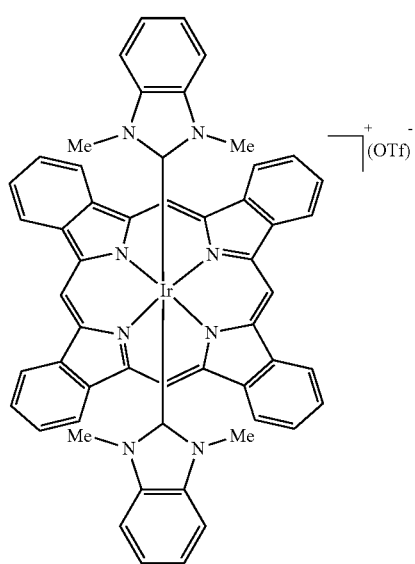
Complex 110
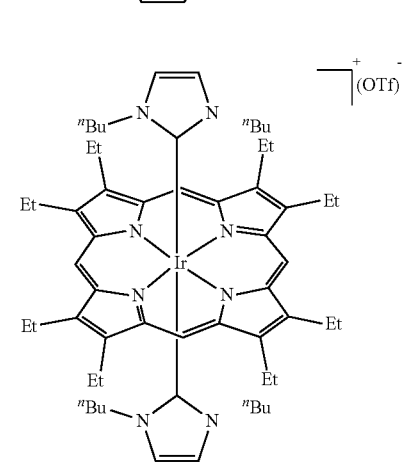
Preparation and Characterization of the Ir(III)-NHC Complexes
Synthesis of [Ir$^{III}$(ttp)(IMe)$_2$](ORf) (Complex 101):
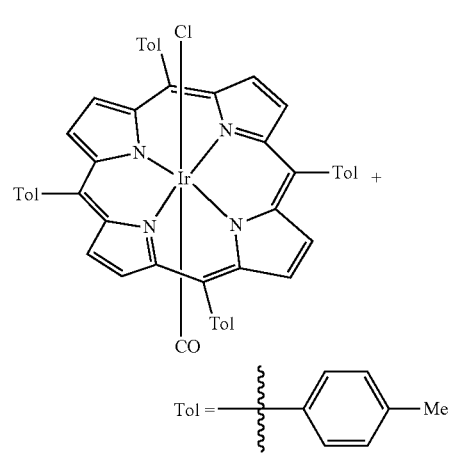

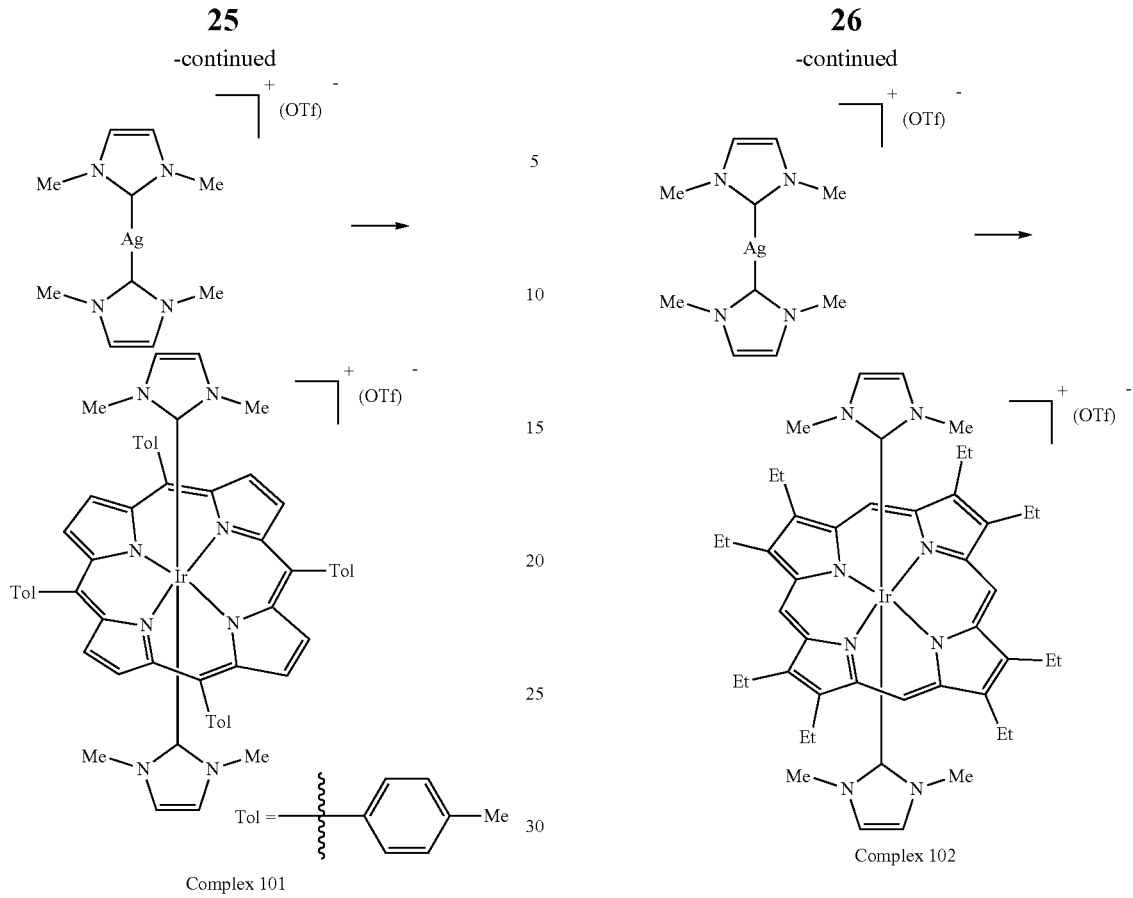

Complex 101

Complex 102

To a CH$_2$Cl$_2$ solution (10 mL) of [Ir$^{III}$(ttp)Cl(CO)] (0.08 mmol, 1 equiv.), [Ag(IMe)$_2$](OTf) (1.05 equiv.) was added. The mixture was stirred at room temperature for 18 hours. The reaction mixture was concentrated under reduced pressure. The desired complex was purified by flash column chromatography on silica gel using CH$_2$Cl$_2$/EtOAc (1:1-1:4 v/v) as eluent.

Yield: 96%. $^1$H NMR (400 MHz, CDCl$_3$) δ 8.61 (s, 8H), 7.64 (d, J=7.6 Hz, 8H), 7.46 (d, J=7.8 Hz, 8H), 4.83 (s, 4H), 2.63 (s, 12H), −0.57 (s, 12H). $^{13}$C NMR (125 MHz, CDCl$_3$) ν=136.3 (Ir—C$_{NHC}$). $^{19}$F NMR (376 MHz, CDCl$_3$) δ-78.5 (OTf). IR (KBr disc, cm$^{-1}$): ν=1031 (OTf), 1018 ("oxidation state marker band"). FAB-MS (m/z): 1053 [M]$^+$. Elemental analysis calcd. (%) for C$_{59}$H$_{52}$F$_3$IrN$_8$O$_3$S: C 58.94, H 4.36, N 9.32; Found C 59.02, H 4.47, N 9.01.

Synthesis of [Ir$^{III}$(oep)(IMe)$_2$](OTf) (Complex 102):

To a CH$_2$Cl$_2$ solution (10 mL) of [Ir$^{III}$(oep)Cl(CO)] (0.08 mmol, 1 equiv.), [Ag(IMe)$_2$](OTf) (1.05 equiv.) was added. The mixture was stirred at room temperature for 12 hours. The reaction mixture was concentrated under reduced pressure. The desired complex was purified by flash column chromatography on silica gel using CH$_2$Cl$_2$/EtOAc (1:1-1:4 v/v) as eluent.

Yield: 88%. $^1$H NMR (400 MHz, CDCl$_3$) δ 9.39 (s, 4H), 4.53 (s, 4H), 3.89 (q, J=7.6 Hz, 16H), 1.82 (t, J=7.6 Hz, 24H), −0.96 (s, 12H). $^{13}$C NMR (125 MHz, CDCl$_3$) δ 135.8 (Ir—C$_{NHC}$). $^{19}$F NMR (376 MHz, CDCl$_3$) δ-78.5 (OTf). IR (KBr disc, cm$^{-1}$): ν=1031 (OTf), 1022 ("oxidation state marker band"). FAB-MS (m/z): 917 [M]$^+$. Elemental analysis calcd. (%) for C$_{47}$H$_{60}$F$_3$IrN$_8$O$_3$S: C 52.94, H 5.67, N 10.51; Found C 52.54, H 5.63, N 10.31.

Synthesis of [Ir$^{III}$(oep)(I$^i$Pr)$_2$](PF$_6$) (Complex 103):

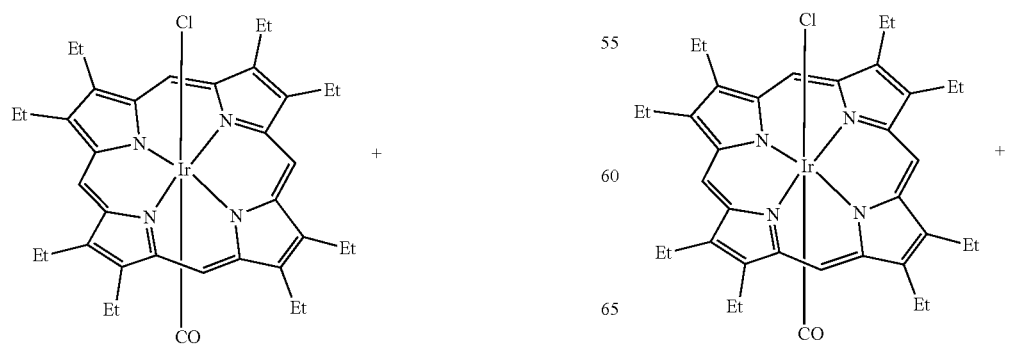

-continued

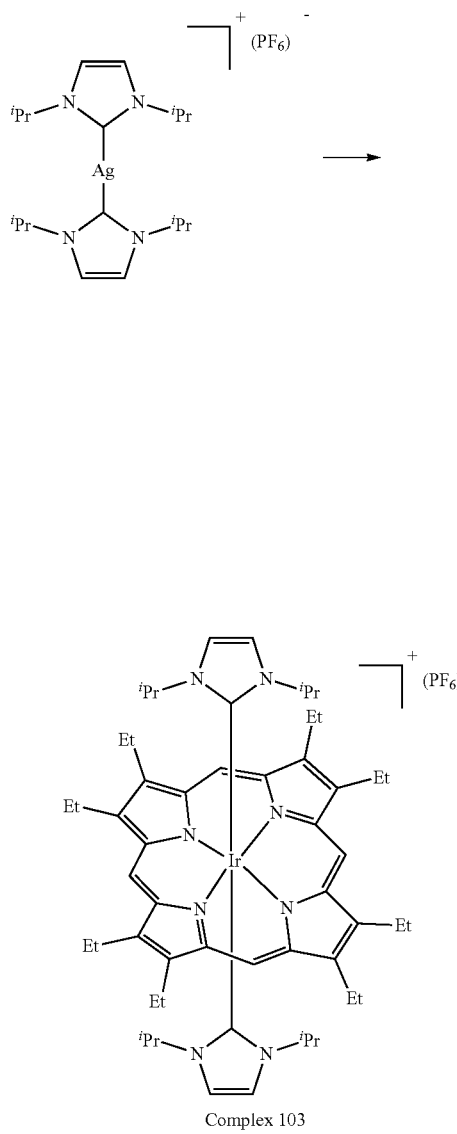

Complex 103

Synthesis of [Ir$^{III}$(F$_{20}$tpp)(IMe)$_2$](OTf) (Complex 104):

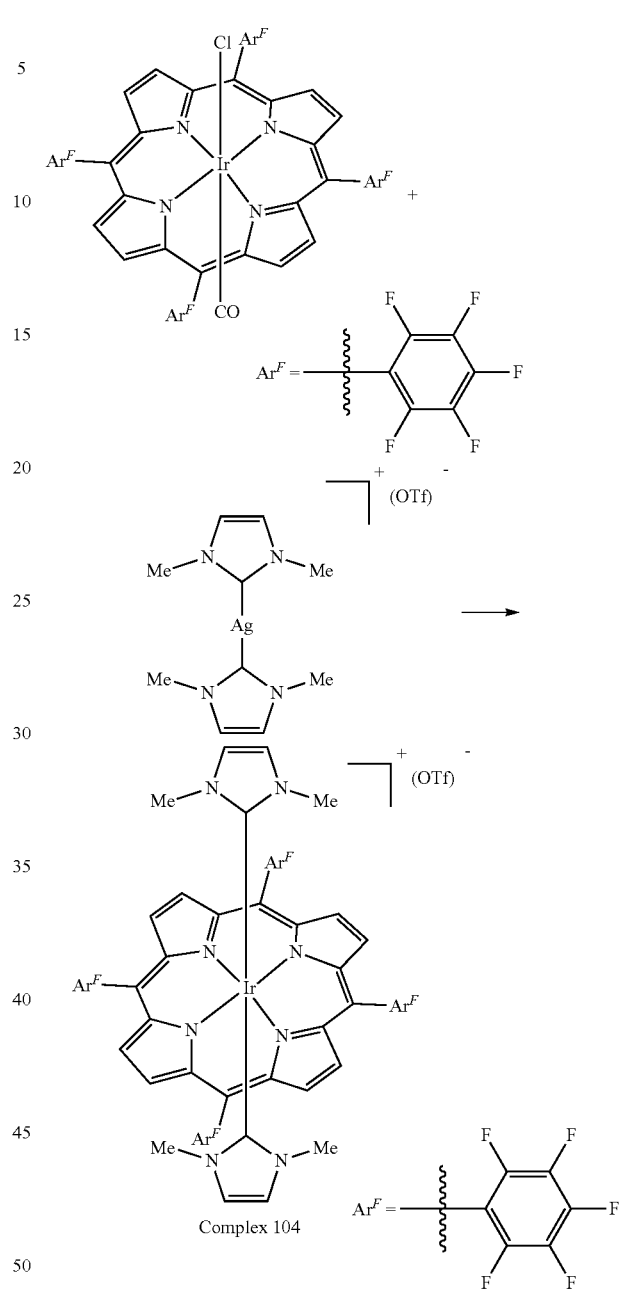

Complex 104

To a CH$_2$Cl$_2$ solution (10 mL) of [Ir$^{III}$(oep)Cl(CO)] (0.08 mmol, 1 equiv.), [Ag(I$^i$Pr)$_2$](OTf) (1.05 equiv.) was added. The mixture was stirred at room temperature for 12 hours. The reaction mixture was concentrated under reduced pressure. The desired complex was purified by flash column chromatography on silica gel using CH$_2$Cl$_2$/EtOAc (1:1-1:4 v/v) as eluent.

Yield: 85%. $^1$H NMR (400 MHz, CDCl$_3$) δ 9.40 (s, 4H), 4.84 (s, 4H), 3.95-3.80 (m, 16H), 1.88 (t, J=7.6 Hz, 24H), −0.67 (d, J=6.7 Hz, 24H), −3.14 (sep, J=6.7 Hz, 4H). $^{13}$C NMR (125 MHz, CDCl$_3$) δ 132.4 (Ir—C$_{NHC}$). $^{19}$F NMR (376 MHz, CDCl$_3$) δ-73.2, −75.1 (PF$_6^-$). IR (KBr disc, cm$^{-1}$): ν=1022 ("oxidation state marker band"), 839 (PF$_6^-$). FAB-MS (m/z): 1029 [M]$^+$. Elemental analysis calcd. (%) for C$_{54}$H$_{76}$F$_6$IrN$_8$P: C 55.23, H 6.52, N 9.54; Found C 55.01, H 6.55, N 9.28.

To a CH$_2$Cl$_2$ solution (10 mL) of [Ir$^{III}$(F$_{20}$tpp)Cl(CO)] (0.08 mmol, 1 equiv.), [Ag(IMe)$_2$](OTf) (2.1 equiv.) was added. The mixture was stirred at room temperature for 4 days. The reaction mixture was concentrated under reduced pressure. The desired complex was purified by flash column chromatography on silica gel using CH$_2$Cl$_2$/EtOAc (1:1-1:4 v/v) as eluent.

Yield: 70%. $^1$H NMR (400 MHz, CD$_2$Cl$_2$) δ8.70 (s, 8H), 4.76 (s, 4H), −0.55 (s, 12H). $^{13}$C NMR (125 MHz, CD$_2$Cl$_2$) δ 133.7 (Ir—C$_{NHC}$). $^{19}$F NMR (376 MHz, CD$_2$Cl$_2$) δ-78.5 (OTf), −138.3 (dd), −149.6 (t), −160.0 (td). IR (KBr disc, cm$^{-1}$): ν=1031 (OTf$^-$), 1019 ("oxidation state marker band"). FAB-MS (m/z): 1356 [M]$^+$. Elemental analysis calcd. (%) for C$_{55}$H$_{24}$F$_{23}$IrN$_8$O$_3$S: C 43.86, H 1.61, N 7.44; Found C 43.69, H 1.62, N 7.38.

Synthesis of [Ir^III(ttp)(BIMe)₂](OTf) (Complex 105):

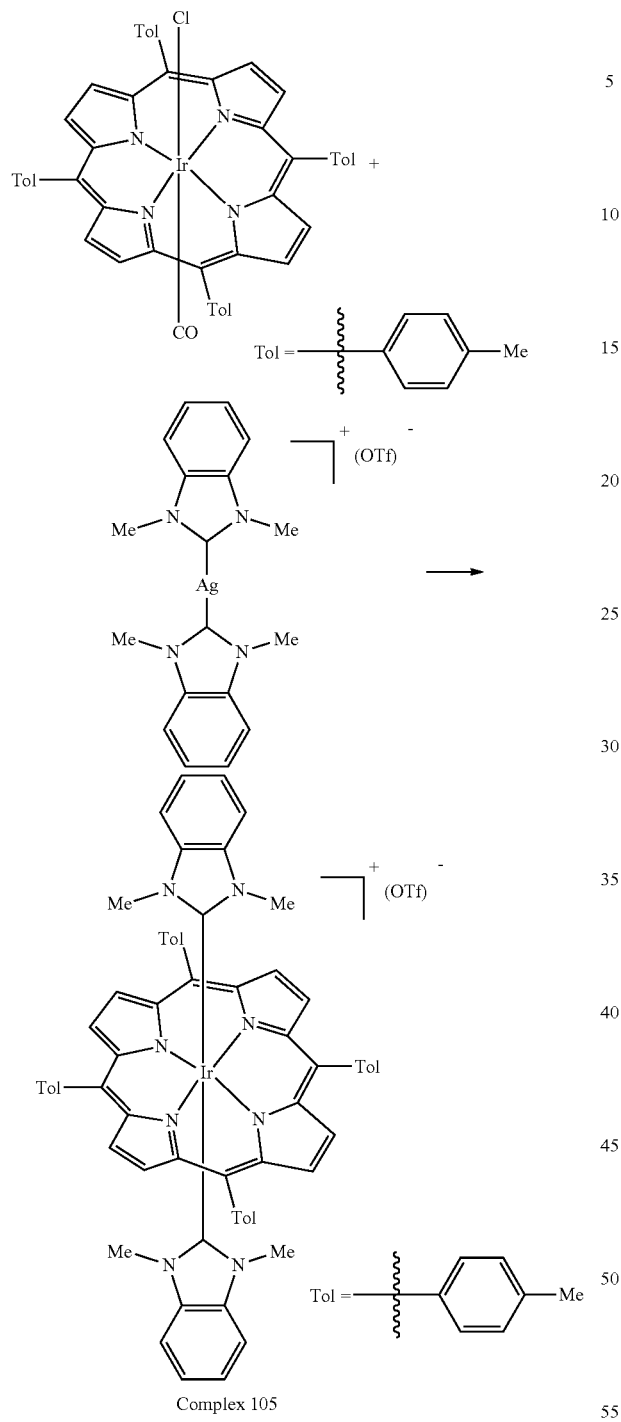

Complex 105

To a CH₂Cl₂ solution (10 mL) of [Ir^III(ttp)Cl(CO)] (0.08 mmol, 1 equiv.), [Ag(BIMe)₂](OTf) (1.05 equiv.) was added. The mixture was stirred at room temperature for 18 hours. The reaction mixture was concentrated under reduced pressure. The desired complex was purified by flash column chromatography on silica gel using CH₂Cl₂/EtOAc (1:1-1:4 v/v) as eluent.

Yield: 90%. $^1$H NMR (400 MHz, CDCl₃) δ 8.69 (s, 8H), 7.54 (d, J=7.9 Hz, 8H), 7.42 (d, J=7.9 Hz, 8H), 6.64-6.62 (m, 4H), 6.10-6.07 (m, 4H), 2.60 (s, 12H), −0.41 (s, 12H). $^{13}$C NMR (125 MHz, CDCl₃) δ 147.1 (Ir—$C_{NHC}$). $^{19}$F NMR (376 MHz, CDCl₃) δ −78.5 (OTf⁻). IR (KBr disc, cm⁻¹): ν=1030 (OTf⁻), 1018 ("oxidation state marker band"). FAB-MS (m/z): 1153 [M]⁺. Elemental analysis calcd. (%) for C₆₇H₅₆F₃IrN₈O₃S: C 61.78, H 4.33, N 8.60; Found C 61.97, H 4.40, N 8.42.

Synthesis of [Ir^III(oep)(BIMe)₂](OTf) (Complex 106):

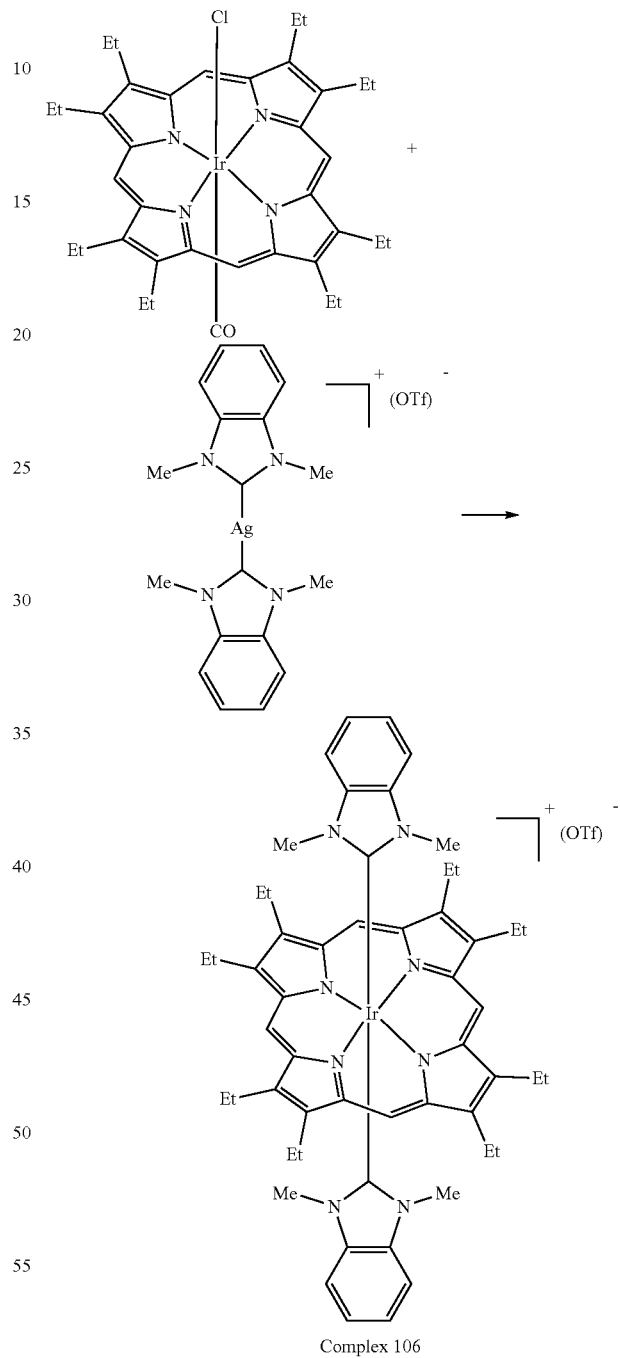

Complex 106

To a CH₂Cl₂ solution (10 mL) of [Ir^III(oep)Cl(CO)] (0.08 mmol, 1 equiv.), [Ag(BIMe)₂](OTf) (1.05 equiv.) was added. The mixture was stirred at room temperature for 12 hours. The reaction mixture was concentrated under reduced pressure. The desired complex was purified by flash column chromatography on silica gel using CH₂Cl₂/EtOAc (1:1-1:4 v/v) as eluent.

Yield: 87%. $^1$H NMR (400 MHz, CDCl$_3$) δ 9.45 (s, 4H), 6.49-6.48 (m, 4H), 5.92-5.88 (m, 4H), 3.91 (q, J=7.6 Hz, 16H), 1.83 (t, J=7.6 Hz, 24H), −0.82 (s, 12H). $^{13}$C NMR (125 MHz, CDCl$_3$) δ 147.1 (Ir—C$_{NHC}$). $^{19}$F NMR (376 MHz, CDCl$_3$) δ −78.5 (OTf). IR (KBr disc, cm$^{-1}$): ν=1031 (OTf), 1020 ("oxidation state marker band"). FAB-MS (m/z): 1017 [M]$^+$. Elemental analysis calcd. (%) for C$_{55}$H$_{64}$F$_3$IrN$_8$O$_3$S: C 56.63, H 5.53, N 9.61; Found C 56.92, H 5.43, N 9.65

Photophysical properties of the Ir(III)-NHC complexes

TABLE 1

UV-visible absorption and emission data

| Complex | UV-vis absorption data$^a$ λ$_{max}$/nm (log ε) | Emission data$^a$ Solution at 298K λ$_{max}$/nm (τ/μs) | Φ$_{em}$[×10$^{-2}$] |
|---|---|---|---|
| [Ir$^{III}$(oep)Cl(CO)] | 342 (4.44), 403 (5.38), 518 (4.30), 549 (4.62) | 666 (83.3), 722 (sh) | 5.03 |
| [Ir$^{III}$(oep)(CNPhOMe)$_2$](BF$_4$) | 266 (4.70), 344(sh) | 663 | 6.40 |
| 101 | (4.36), 395 (5.20), 515 (4.17), 547 (4.50) | (124.7), 717(sh) | 0.41 |
| 102 | 374 (4.76), 438 (5.12), 547 (3.87), 620 (3.82) | non-emissive | 0.03 |
| 103 | (br)$^b$ 351 (sh) (4.52), 372 (4.86), 429 (4.89), 532 (4.10), 556 (4.01) | 701 (2.7), 766 (sh) 701 (1.9), | 0.08 |
| 104 |  | / |  |
| 105 |  |  | 0.66 |
| 106 | 353 (sh) (4.49), 375 (4.82), 432 (4.82), 537 ((4.09), 560 4.02) 355 (sh) (4.63), 374 (4.89), 418 (sh) (4.72), 440 (5.00), 537 (4.13), 297 (4.63), 372 (4.63), 437 (4.99), 564 (3.85) | 763 (sh) 754 (0.5), 829 (sh) non-emissive 701 (3.6), 765 (sh) |  |

TABLE 1-continued

UV-visible absorption and emission data

| Complex | UV-vis absorption data$^a$ λ$_{max}$/nm (log ε) | Emission data$^a$ Solution at 298K λ$_{max}$/nm (τ/μs) | Φ$_{em}$[×10$^{-2}$] |
|---|---|---|---|
|  | (br)$^b$, 611 (3.87) (br)$^b$ 297 (4.42), 373, (4.76), 428 (4.82), 533 (4.03), 557 (3.95) |  |  |

$^a$Measurements was performed in degassed CHCl$_3$. $^b$Broad absorption band spans from ca. 510 to 670 nm. $^c$Measurements was performed in degassed CH$_2$Cl$_2$.

Complexes 101-106 absorb strongly in the visible light region and some of which are emissive in the near IR region.

Anticancer Properties

Cationic iridium(III) porphyrin complexes bearing bis-NHC ligands were found to show superior cytotoxicity to that of cisplatin towards a panel of human cancer cell lines. Complexes 101, 102, 103 and 104 exhibit potent cytotoxicity with submicromolar IC$_{50}$ values, while [Ir$^{III}$(ope)(CNPhOMe)$_2$](BF$_4$) shows reduced cytotoxicity (Table 2). Among the bis-NHC complexes, the higher cellular uptake of Complex 102 (with octaethylporphyrin) than that of 101 (with meso-tetratolylporphyrin) and Complex 104 (with meso-tetrakis(pentafluorophenyl)porphyrin) results in higher cytotoxicity towards different cancer cell lines. In addition, the charge-neutral [Ir$^{III}$(oep)Cl(CO)], which showed the lowest cellular uptake and lipophilicity, is relatively noncytotoxic, with an IC$_{50}$ value>50 μM to the NCI-H460 lung cancer cell line. These findings highlight that the cationic character and porphyrin scaffold of iridium (III) bis-NHC complexes are crucial for facilitating efficient accumulation in cells for anticancer activities.

TABLE 2

In vitro cytotoxicity of the selected iridium(III) porphyrin complexes against a panel of human cancer cell lines.$^{a-c}$

| | IC$_{50}$ (μM)$^b$ | | | | |
|---|---|---|---|---|---|
| | HeLa | HepG2 | MCF-7 | HCT116 | HCC827 |
| Complex 101 | 0.17$^{±0.1}$ | 2.1$^{±0.3}$ | 0.65$^{±0.2}$ | 0.14$^{±0.04}$ | 2.29$^{±0.50}$ |
| Complex 102 | 0.03$^{±0.01}$ | 0.93$^{±0.1}$ | 0.16$^{±0.1}$ | 0.14$^{±0.1}$ | 1.1$^{±0.3}$ |
| Complex 103 | 0.10$^{±0.1}$ | 2.4$^{±0.2}$ | 0.73$^{±0.5}$ | 0.11$^{±0.03}$ | 0.69$^{±0.01}$ |
| Complex 104 | 0.10$^{±0.1}$ | 0.94$^{±0.1}$ | 0.26$^{±0.1}$ | 0.4$^{±0.2}$ | 1.23$^{±0.10}$ |
| [Ir$^{III}$(ope)(CNPhOMe)$_2$](BF$_4$) | 7.9$^{±0.5}$ | >100 | >100 | 23$^{±3.3}$ | 50$^{±3.6}$ |
| [Ir$^{III}$(oep)Cl(CO)] | / | / | / | / | / |
| Cisplatin | 12.31$^{±3.31}$ | 35.78$^{±7.66}$ | 20.94$^{±5.23}$ | 12.19$^{±4.73}$ | 14.35$^{±3.46}$ |

| | IC$_{50}$ (μM) | | | | |
|---|---|---|---|---|---|
| | NCI-H460 (dark) | NCI-H460 (light) | PI$^c$ | Uptake$^d$ | Log P$^e$ |
| Complex 101 | 1.22$^{±0.03}$ | 0.11$^{±0.08}$ | 11.1 | 147.6$^{±6.4}$ | 3.03 |
| Complex 102 | 0.15$^{±0.05}$ | 0.009$^{±0.004}$ | 16.7 | 309.7$^{±46.7}$ | 2.96 |
| Complex 103 | 0.16$^{±0.04}$ | 0.006$^{±0.002}$ | 26.7 | 158.7$^{±29.5}$ | 3.23 |
| Complex 104 | 0.31$^{±0.04}$ | 0.03$^{±0.002}$ | 10.3 | 131.3$^{±10.2}$ | 2.76 |
| [Ir$^{III}$(ope)(CNPhOMe)$_2$](BF$_4$) | 2.9$^{±0.02}$ | 0.12$^{±0.02}$ | 24.2 | 116.2$^{±20.6}$ | 2.81 |
| [Ir$^{III}$(oep)Cl(CO)] | >50 | 19.70$^{±1.0}$ | >2.5 | 34.1$^{±2.8}$ | 2.38 |
| Cisplatin | 13$^{±0.4}$ | 18$^{±1.6}$ | 0.72 | / | / |

$^a$HeLa = cervical epithelial carcinoma; HepG2 = hepatocellular carcinoma; MCF-7 = breast carcinoma; HCT-116 = colorectal carcinoma; HCC827 = non-small cell lung carcinoma; NCI-H460 = non-small cell lung carcinoma.
$^b$IC$_{50}$ values were examined by MTT assay after incubation of drugs for 72 h.
$^c$PI = IC$_{50}$(dark)/IC$_{50}$(light).
$^d$Cellular uptake was determined by the iridium content (μg) in the cellular proteins (g) after treatment of the NCI-H460 cells with each complex (1 μM) for 2 h.
$^e$Lipophilicity was determined by measuring the ratio of the amount of iridium (μg) in each complex partitioned in n-octanol and saline solution (0.9% w/v).

Figure 5:
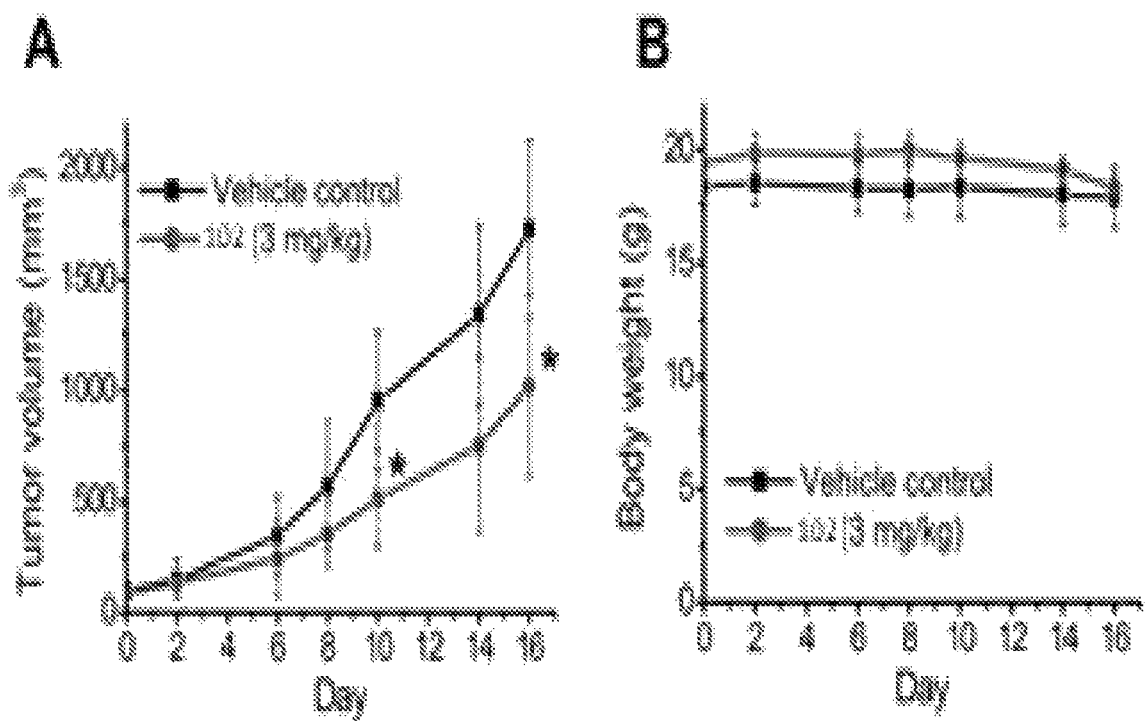
Figure 6:
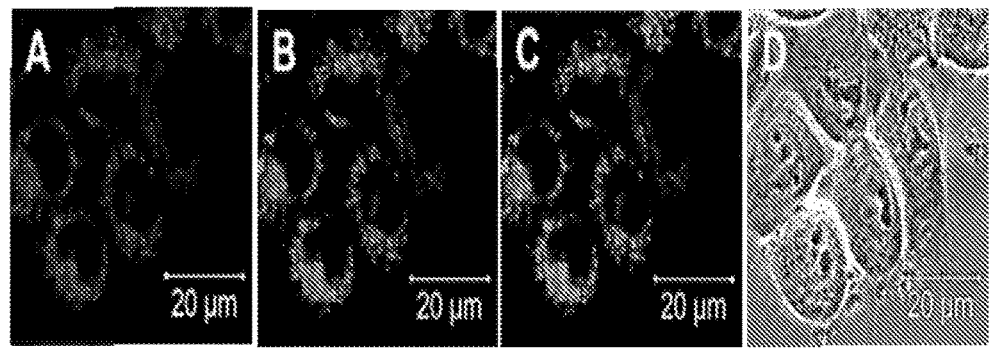
Figure 11:
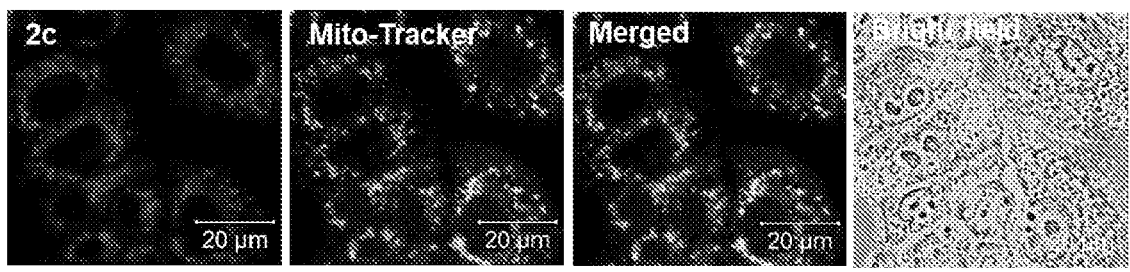
Figure 11:
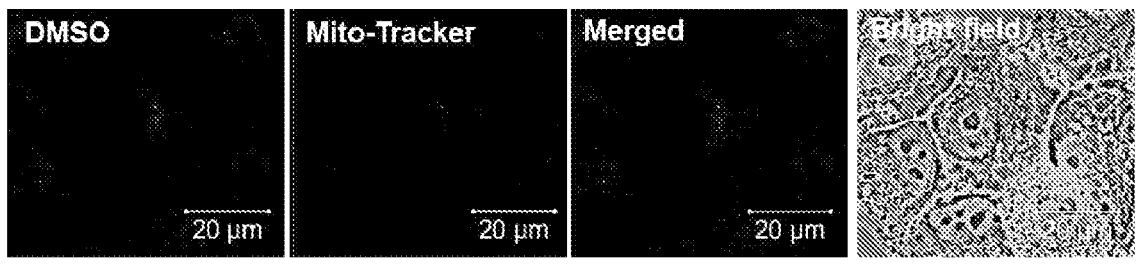
Figure 12:
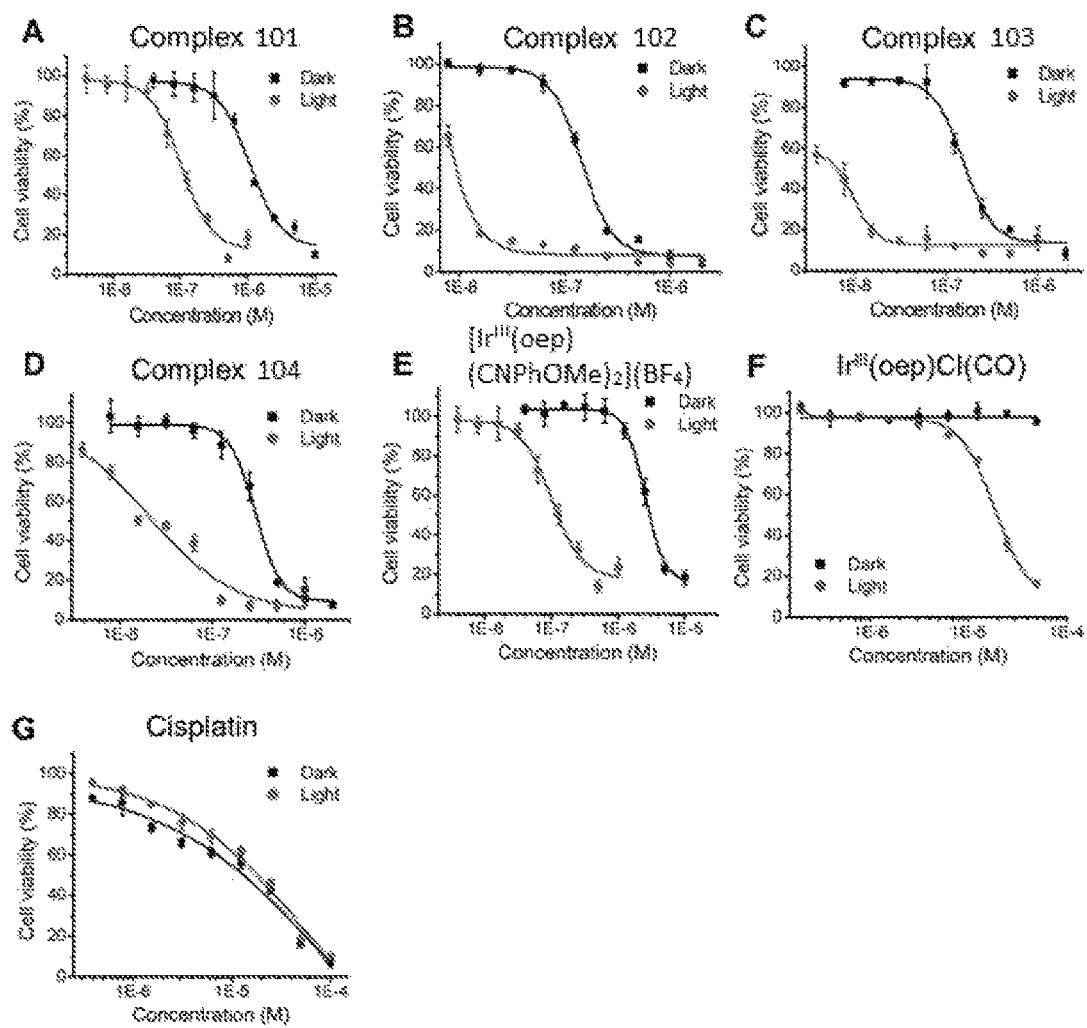

On the basis of the potent in vitro cytotoxicity of Complex 102, its in vivo antitumor properties were examined. Nude mice bearing NCI-H460 human non-small cell lung cancer xenografts were administered 102 (3 mg/kg) via intravenous injection thrice weekly. The tumor size was reduced by 41% after a 16-day treatment without apparent toxicity, including body weight loss and death (FIG. 5). In view of the advantageous photophysical properties (including high emission quantum yield and long-lived electronic excited state) of Complex 102 among the bis-NHC iridium(III) complexes, cellular imaging of Complex 102 was performed to examine its subcellular localization in NCI-H460 cells. As shown in FIG. 6, the resulting images clearly revealed that the red-emitting Complex 102 mainly colocalized with the green-emitting stain of the endoplasmic reticulum (ER-Tracker) with a high Pearson's correlation coefficient (R) of 0.903 (FIG. 10). In contrast, a relatively poor overlap was observed between the fluorescence images of the complex and Mito-Tracker green, with an R-value of 0.548 (FIG. 11). These findings indicated that Complex 102 accumulated mainly in the ER and only somewhat in the mitochondria in NCI-H460 cells and may elicit cytotoxic actions through the induction of ER stress-associated mechanisms of cell death.

Photocytotoxicity

Prompted by the finding that the iridium(III) porphyrin complexes are excellent singlet oxygen photosensitizers, we examined their photocytotoxicity. NCI-H460 lung cancer cells incubated with the complexes were exposed to a low dose of visible light irradiation (2.8 mW cm$^{-2}$) for 1 h. The cytotoxicity of the iridium(III) porphyrin complexes increased markedly by 10- to 27-fold upon irradiation, and [Ir$^{III}$(oep)(I$^i$Pr)$_2$](PF$_6$) (Complex 103) showed the largest enhancement among the complexes examined (Table 2 and FIG. 12). [Ir$^{III}$(oep)(IMe)$_2$](OTf) (Complex 102) and [Ir$^{III}$(oep)(I$^i$Pr)$_2$](PF$_6$) (Complex 103) exhibited very potent cytotoxicity with nanomolar IC$_{50}$ values. The cytotoxicity of [Ir$^{III}$(oep)Cl(CO)] was also evaluated for comparison. This complex is relatively noncytotoxic in the dark with an IC$_{50}$ value>50 mM and increased to 19.7±1.0 mM upon visible light irradiation. For cisplatin, the difference in the phototoxicity index (PI) was <1, indicating an absence of photoinduced cytotoxicity under our experimental conditions. Thus, the cytotoxicity of the iridium(III)porphyrin complexes with the incorporation of axial bis-carbene ligands is significantly enhanced under light irradiation.

Figure 7:
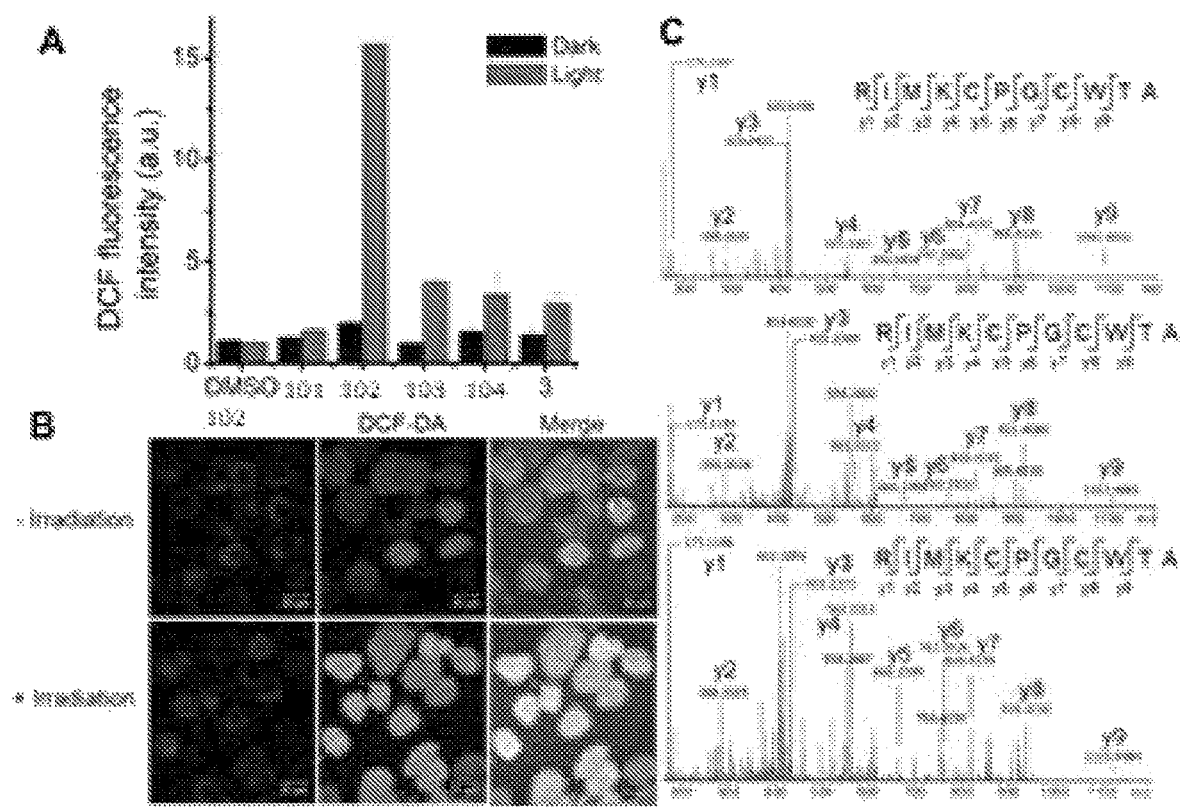

To examine the relationship between photocytotoxicity and the photosensitizing properties of the complexes, we measured the cellular reactive oxygen species (ROS) generation using the ROS probe H$_2$DCF-DA after treatment of cancer cells with the iridium(III) porphyrin complexes. As shown in FIG. 7, no significant change in DCF fluorescence was observed in NCI-H460 lung cancer cells incubated with the complexes in the dark. Exposure to visible light irradiation resulted in increased DCF fluorescence intensity, revealing elevated cellular ROS levels. In particular, a 10-fold elevation in ROS levels in cells treated with Complex 102 was observed. The result was further corroborated by the strong green fluorescence observed from DCF when cells were treated with Complex 102 followed by light irradiation (FIG. 7b). These results confirmed the generation of ROS, possibly $^1$O$_2$, in NCI-H460 cells treated with Ir(III) complexes upon visible light irradiation.

We further examined the possibility of protein oxidation as a consequence of photoinduced oxidative stress caused by Complex 102. A peptide (RIMKCPGCWTA) from thioredoxin (Trx) was employed as a model to investigate the possible oxidative modification sites by electrospray ionization tandem mass spectrometry (ESI-MS/MS). The peptide was found to undergo oxidative modifications in the presence of Complex 102 upon irradiation. Three different types of oxidized products, including the formation of a disulfide bridge and the oxidation of the sulfur atoms of cysteine and methionine, were characterized (FIG. 7C, FIG. 14 and Tables 4-6). The peptide alone as a control was shown to remain unchanged when incubated in the dark or upon light irradiation (FIG. 13 and Table 3). As shown in FIG. 7C and FIG. 14, three triply charged species were detected with mass differences of −0.671 (top), +4.660 (middle) and +10.662 (bottom) Da, respectively, from the unmodified peptide. Further MS/MS analysis revealed that the most intense peak (m/z 421.8638; FIG. 7C (top), Table 4) corresponds to the formation of an intramolecular disulfide bond, in which the resulting fragment y5 and y8 ions bearing free cysteine and cysteine thioaldehyde residues, respectively, were observed.

TABLE 3

Mass errors of the fragments detected from Trx peptide (RIMKCPGCWTA) at m/z 422.54 by ESI-MS/MS.

| Assignment | Observed (m/z) | Theoretical (m/z) | Mass error (ppm) |
| --- | --- | --- | --- |
| [y1]$^+$ | 175.1190 | 175.1195 | −2.86 |
| [y2]$^+$ | 288.2030 | 288.2036 | −2.08 |
| [y3]$^+$ | 419.2430 | 419.2441 | −2.62 |
| [y4]$^+$ | 547.3376 | 547.3390 | −2.56 |
| [y5]$^+$ | 650.3467 | 650.3482 | −2.31 |
| [y6]$^+$ | 747.3996 | 747.4010 | −1.87 |
| [y7]$^+$ | 804.4212 | 804.4224 | −1.49 |
| [y8]$^+$ | 907.4299 | 907.4316 | −1.87 |
| [y9]$^+$ | 1093.5084 | 1093.5109 | −2.29 |

TABLE 4

Mass errors of the fragments detected from modified Trx peptide (RIMKCPGCWTA) at m/z 421.86 by ESI-MS/MS. BOLD label represents the site for disulfide bond formation.

| Assignment | Observed (m/z) | Theoretical (m/z) | Mass error (ppm) |
| --- | --- | --- | --- |
| [y1]$^+$ | 175.1187 | 175.1195 | −4.57 |
| [y2]$^+$ | 288.2025 | 288.2036 | −3.82 |
| [y3]$^+$ | 419.2423 | 419.2441 | −4.29 |
| [y4]$^+$ | 547.3367 | 547.3390 | −4.20 |
| [y5]+ | 650.3456 | 650.3476 | −3.08 |
| [y6]$^+$ | 747.3982 | 747.4004 | −2.94 |
| [y7]$^+$ | 804.4197 | 804.4218 | −2.61 |
| [y8]+ | 905.4135 | 905.4154 | −2.10 |
| [y9]$^+$ | 1091.4931 | 1091.4947 | −1.47 |

TABLE 5

Mass errors of the fragments detected from modified Trx peptide (RMKCPGCWTA) at m/z 427.20 by ESI-MS/MS. UNDERLINE label indicates the oxidative site and BOLD label represents the site for disulfide bond formation.

| Assignment | Observed (m/z) | Theoretical (m/z) | Mass error (ppm) |
| --- | --- | --- | --- |
| [y1]$^+$ | 175.1185 | 175.1195 | −5.71 |
| [y2]$^+$ | 288.2024 | 288.2036 | −4.16 |
| [y3+O]$^+$ | 435.2369 | 435.2384 | −3.45 |
| [y4]$^+$ | 563.3312 | 563.3333 | −3.73 |
| [y5]+ | 666.3409 | 666.3426 | −2.55 |
| [y6]$^+$ | 763.3931 | 763.3953 | −2.88 |
| [y7]$^+$ | 820.4142 | 820.4167 | −3.05 |

TABLE 5-continued

Mass errors of the fragments detected from modified Trx peptide (RMKCPGCWTA) at m/z 427.20 by ESI-MS/MS. UNDERLINE label indicates the oxidative site and BOLD label represents the site for disulfide bond formation.

| Assignment | Observed (m/z) | Theoretical (m/z) | Mass error (ppm) |
|---|---|---|---|
| [y8]+ | 921.4080 | 921.4103 | −2.50 |
| [y9]+ | 1107.4881 | 1107.4896 | −1.35 |

TABLE 6

Mass errors of the fragments detected from modified Trx peptide (RIMKCPGCWTA) at m/z 433.20 by ESI-MS/MS. BOLD label indicates the oxidative site.

| Assignment | Observed (m/z) | Theoretical (m/z) | Mass error (ppm) |
|---|---|---|---|
| [y1]+ | 175.1186 | 175.1195 | −5.14 |
| [y2]+ | 288.2025 | 288.2036 | −3.81 |
| [y3 + O]+ | 435.2375 | 435.2384 | −2.07 |
| [y4]+ | 563.3312 | 563.3333 | −4.05 |
| [y5]+ | 666.3399 | 666.3426 | −4.05 |
| [y6]+ | 763.3926 | 763.3953 | −3.54 |
| [y7]+ | 820.4139 | 820.4168 | −3.53 |
| [y8 + O]+ | 939.4150 | 939.4209 | −6.28 |
| [y9]+ | 1125.4984 | 1125.5002 | −1.60 |

Moreover, additional oxidative modification of the methionine residue to give sulfoxide (y3) with a shift of +16 Da was also found on the disulfide-bridged peptide (m/z 427.1954; FIG. 7C (middle), Table 5). In addition, another oxidation product (m/z 433.1978) with a mass increment of 10.662 in a triply charged state is ascribed to the addition of two oxygen atoms.(32 Da) in the singly charged species. MS/MS sequence analysis displayed the identified y-ions, which are attributed to the oxidized methionine (y3; O-Met, Met 16 Da) and cysteine (y8; O-Cys, Cys 16 Da) of the peptide (FIG. 7C (bottom) and Table 6). These results show that treatment with Complex 102 combined with light activation promoted the oxidation of cysteine and methionine residues through a singlet oxygen-mediated mechanism.

Figure 9:
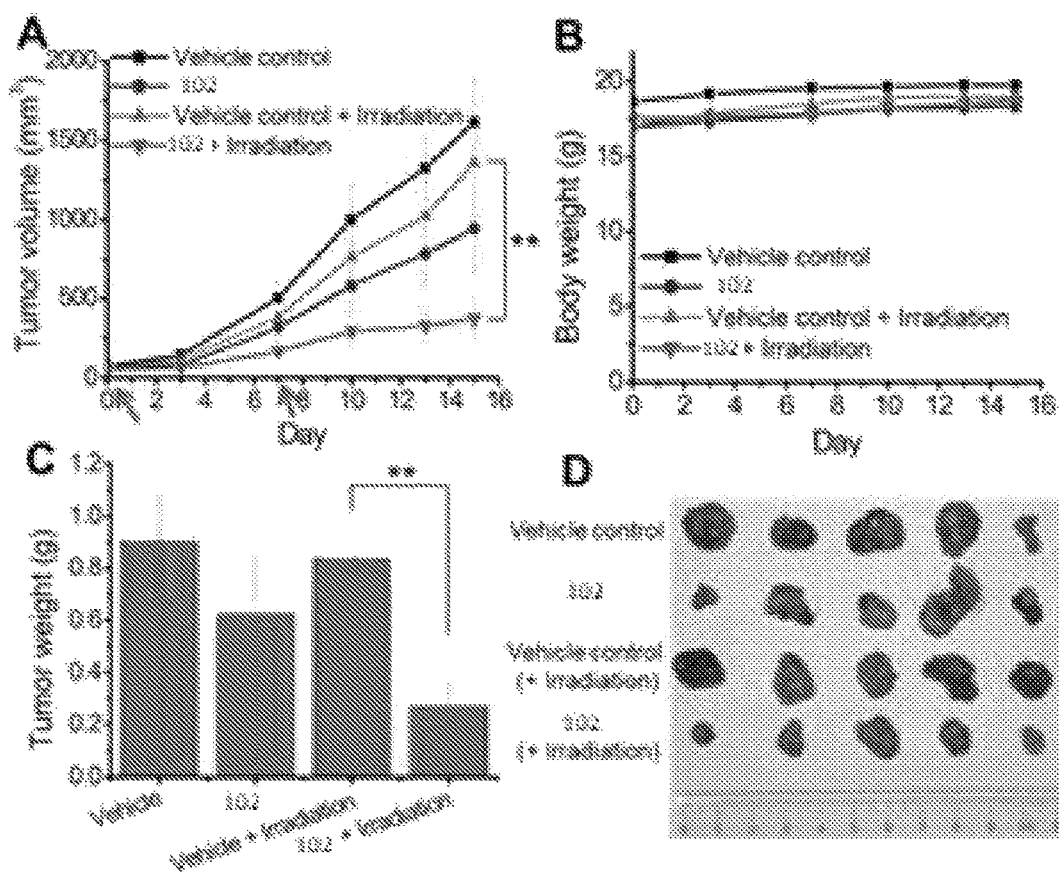

To examine the photoinduced cytotoxicity, the apoptotic cell death and cell cycle progression of the cancer cells treated with Complex 102 and visible light irradiation were analyzed by flow cytometry. NCI-H460 cells were incubated with Complex 102 at 0.1 µM, a concentration that could not lead to strong antiproliferative effects in the dark. Upon exposure to light irradiation, the proportion of cells treated with Complex 102 undergoing apoptotic cell death increased from 5.9% to 81.7%, as shown by the annexin-V-FITC/propidium iodide assay (FIG. 8A). On the other hand, Complex 102 (0.1 µM) did not exhibit a marked effect on the progression of the cell cycle in the dark, showing only a mild increase in the $G_0/G_1$-population from 59.6% to 66.3%. In agreement with the annexin-V/propidium iodide flow cytometry results above, visible light irradiation led to a significant increase in the sub-$G_1$ population (from 2.2% to 96.9%) as a result of extensive DNA fragmentation due to cell death (FIG. 8B). We also examined the antiangiogenic property of Complex 102 in the inhibition of endothelial cell tube formation. As shown in FIG. 8C, moderate inhibition of MS-1 cell tube formation was observed after treatment of the complex in the dark, while tube formation was completely abrogated upon light irradiation. The above results showed that a low dose of Complex 102 causes very low-level cellular damage in the dark but could induce pronounced apoptosis and inhibition of angiogenesis upon visible light irradiation. Noticeably, other iridium porphyrin complexes were also observed to exert similar effects (FIGS. 16, 17, 18). The in vivo photodynamic therapeutic efficacy of complex 102 was also examined. NCI-H460 tumor-bearing mice were divided into four groups, vehicle control, Complex 102 (3.0 mg/kg), vehicle control with irradiation, and Complex 102 (3.0 mg/kg) with irradiation, and subjected to two intratumoral injections of the compounds in a period of 15 days. Mice in the irradiation groups were injected with Complex 102 or solvent vehicle followed by exposure of the tumor site to white light (400-800 nm) at a power density of 110 mW cm$^{-2}$ for 30 min on the first and seventh days. The other two groups of mice received the same treatment without irradiation as a control. As shown in FIG. 9A, the tumor growth of mice treated with Complex 102 and irradiation was markedly decreased by 72% in comparison to that of the vehicle group with light irradiation after only two injections. In contrast, treatment with Complex 102 without irradiation was able to inhibit tumor growth by only 41%. All of the mice displayed negligible changes in body weight throughout the treatment period (FIG. 9B). Moreover, the tumor weight of Complex 102-treated mice in the photoirradiation group was found to be much lower than that in the dark control group (FIG. 9C, 9D), demonstrating the markedly enhanced antitumor efficacy of the combination of dark and photoinduced tumor inhibitory activities.

What is claimed is:
1. A Ir(III) complex comprising a Ir(III)-NHC ligand having a structure of formula I,

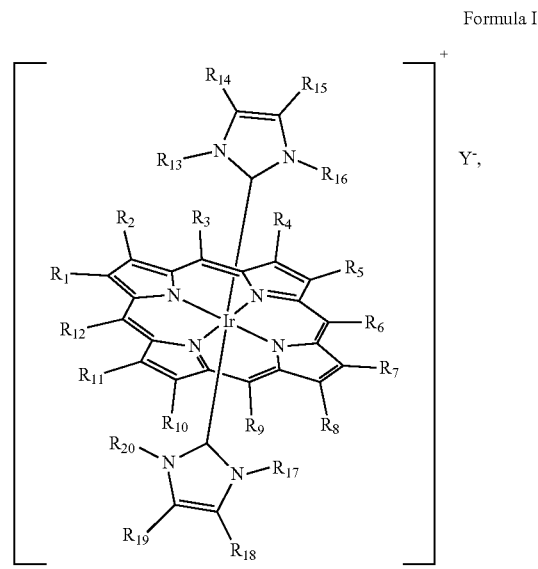

Formula I wherein Ir is a iridium center with an oxidation state of III, $R_1$-$R_{20}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group, wherein each pair of adjacent R groups of $R_1$-$R_{20}$ groups can independently form 5-8 member ring(s) and wherein Y is a counter anion selected from $CF_3SO_3$, $PF_6$, $BF_4$, $BPh_4$, $SbF_6$, Cl, Br or I.

2. The Ir(III) complex of claim 1, wherein $R_3$, $R_6$, $R_9$, and $R_{12}$ groups are

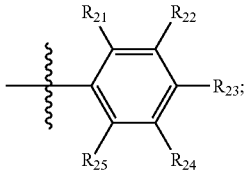

$R_{21}$-$R_{25}$ are independently hydrogen, halogen, unsubstituted alkyl, substituted alkyl, an unsubstituted aryl, a substituted aryl, alkoxy or amino group; $R_1$, $R_2$, $R_4$, $R_5$, $R_7$, $R_8$, $R_{10}$, and $R_{11}$ groups are hydrogen.

3. The Ir(III) complex of claim 1, wherein $R_1$, $R_2$, $R_4$, $R_5$, $R_7$, $R_8$, $R_{10}$ and $R_{11}$ groups are independently halogen, unsubstituted alkyl, substituted alkyl, an unsubstituted aryl, a substituted aryl, alkoxy or amino group; $R_3$, $R_6$, $R_9$ and $R_{12}$ groups are hydrogen.

4. The Ir(III) complex of any one of claim 1, wherein

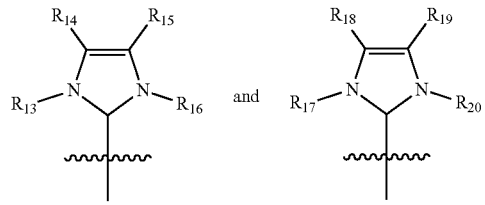

are independently

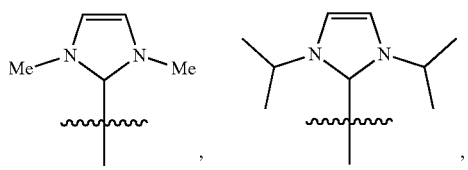

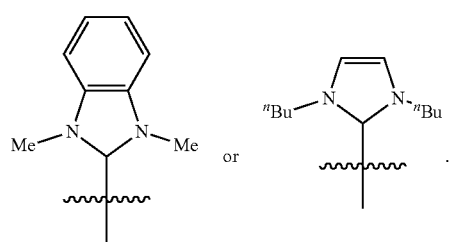

5. The Ir(III) complex of claim 1, wherein the complex comprises a structure selected from:

Complex 101

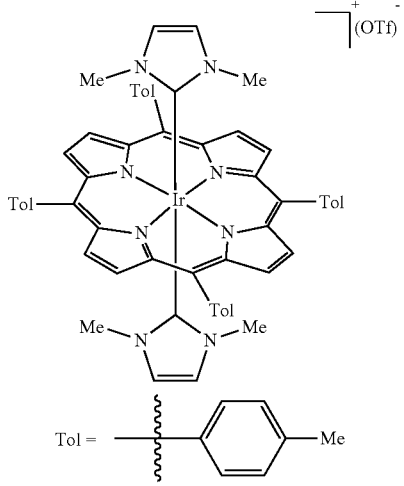

Complex 102

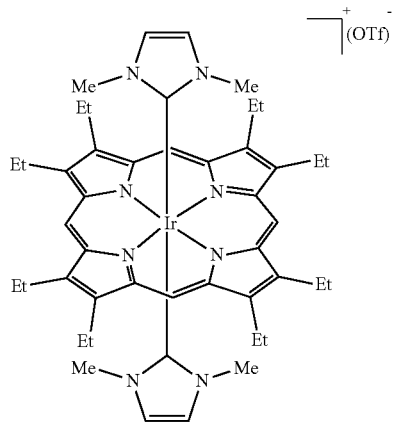

Complex 103

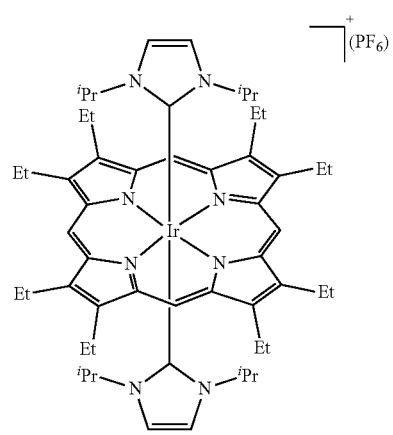

Complex 104
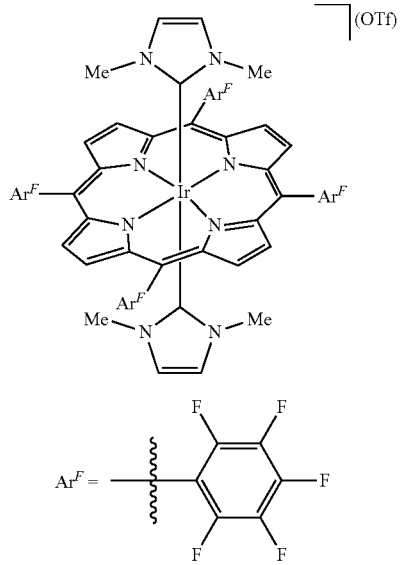
Complex 105
Tol = ⟶⟨benzene⟩—Me
Complex 106
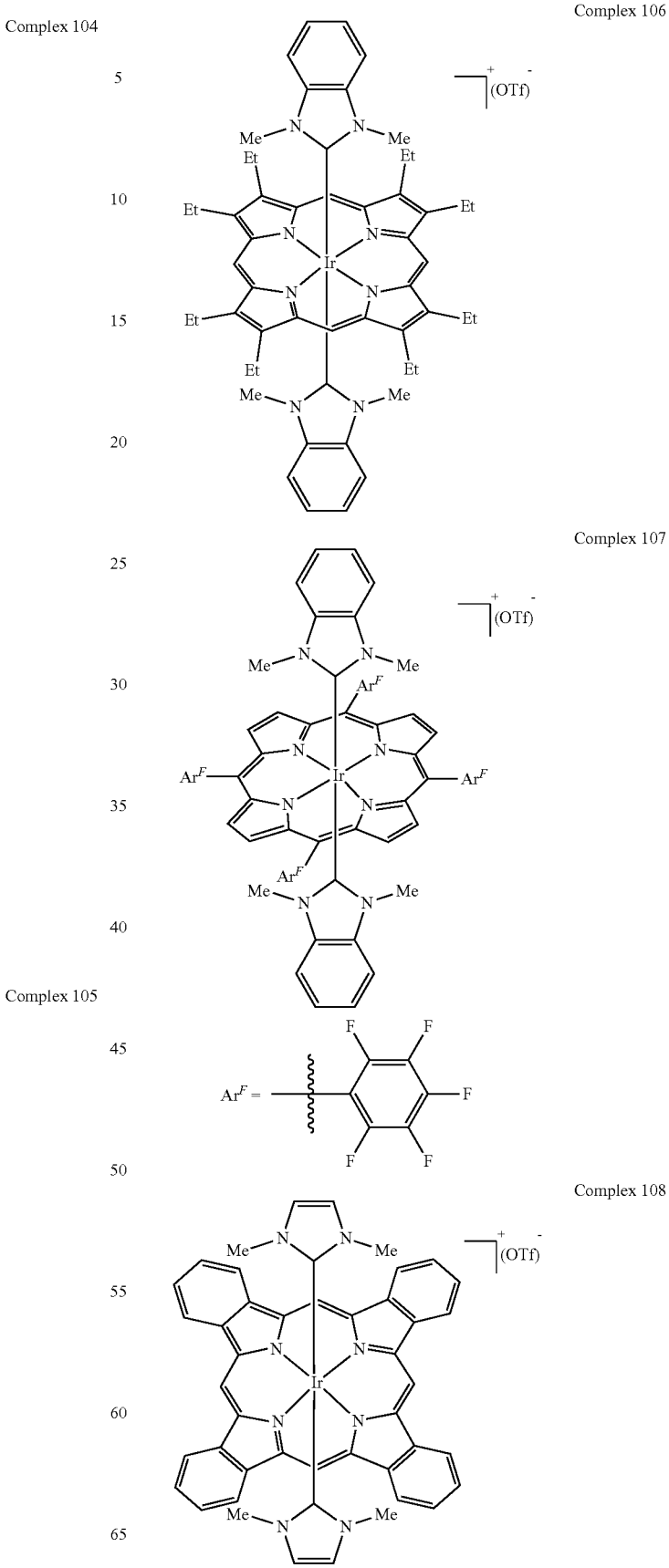
Complex 107
Complex 108

-continued

Complex 109

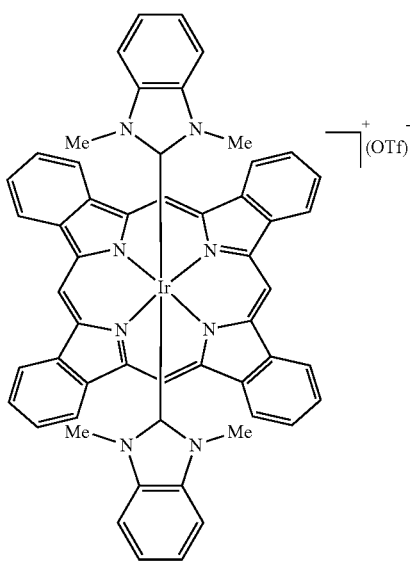

Complex 110

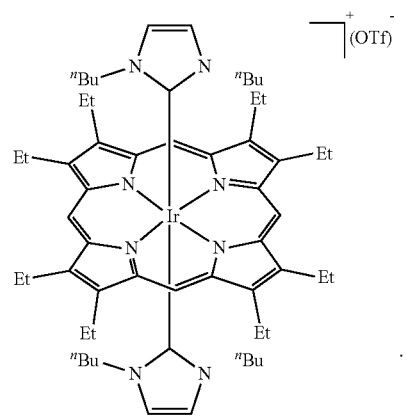

6. A composition comprising the Ir(III) complex of claim 1.

7. The composition of claim 6 wherein the Ir(III) complex has anti-tumor and/or anti-angiogenic properties.

8. A method for treatment of tumor or cancer in a subject comprising administering an effective amount of the composition of claim 6 to the subject in need thereof.

9. The method of claim 8, wherein the tumor is hepatocellular carcinoma, cervical epithelioid carcinoma, lung carcinoma, breast cancer, colon cancer, melanoma or nasopharyngeal carcinoma.

10. The method of claim 8 wherein the treatment comprising induction of cell death, inhibition of cellular proliferation, inhibition of tumor growth in vivo, inhibition of angiogenesis or a combination thereof.

11. The method of claim 8 wherein the effective amount is about 0.1 mg/kg to 50 mg/kg.

12. The method of claim 11 wherein the effective amount is about 2.5-5 mg/kg.

13. The method of claim 8 wherein the treatment occurs in the absence of light irradiation.

14. The method of claim 8 wherein the treatment further comprises irradiating the subject with light.

15. A method to increase the effectiveness of the Ir(III) complex administered to a subject, said method comprises administering an effective amount of Ir(III) complex of claim 1 to the subject and irradiate the subject with light.

16. A method to detect the Ir(III) complex of claim 1 in a subject, said method comprises administering an effective amount of Ir(III) complex to the subject and detect the Ir(III) complex using fluorescent detection.

17. The method of claim 16 wherein the effective amount is 1 µM-500 µM.

\* \* \* \* \*